United States Patent
Nishimura et al.

(10) Patent No.: US 12,195,540 B2
(45) Date of Patent: *Jan. 14, 2025

(54) ANTIBODIES THAT BIND INTEGRIN αvβ8 AND USES THEREOF

(71) Applicant: The Regents of the University of California, Oakland, CA (US)

(72) Inventors: Stephen L. Nishimura, San Francisco, CA (US); Anthony Cormier, San Francisco, CA (US); Saburo Ito, San Francisco, CA (US); Jianlong Lou, San Francisco, CA (US); James D. Marks, San Francisco, CA (US); Yifan Cheng, San Francisco, CA (US); Melody G. Campbell, San Francisco, CA (US); Jody L. Baron, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/153,103

(22) Filed: Jan. 11, 2023

(65) Prior Publication Data

US 2023/0279119 A1 Sep. 7, 2023

Related U.S. Application Data

(63) Continuation of application No. 17/151,009, filed on Jan. 15, 2021, now Pat. No. 11,608,378.

(60) Provisional application No. 62/961,625, filed on Jan. 15, 2020, provisional application No. 63/017,868, filed on Apr. 30, 2020.

(51) Int. Cl.
*A61K 39/00* (2006.01)
*A61K 39/395* (2006.01)
*C07K 16/28* (2006.01)

(52) U.S. Cl.
CPC ...... *C07K 16/2839* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| 9,845,357 B2 | 12/2017 | Nishimura et al. |
| 11,608,378 B2 * | 3/2023 | Nishimura ............ A61P 35/00 |
| 2019/0218298 A1 | 7/2019 | Nishimura |

FOREIGN PATENT DOCUMENTS

| WO | 2014165524 A2 | 10/2014 |
| WO | 2018064478 A1 | 4/2018 |
| WO | 2020051333 A1 | 3/2020 |

OTHER PUBLICATIONS

Application No. EP21741129.7, Extended European Search Report, Mailed On Dec. 12, 2023, 7 pages.
Application No. PCT/US2021/013720, International Preliminary Report on Patentability, Mailed On Jul. 28, 2022, 6 pages.
Application No. PCT/US2021/013720, International Search Report and Written Opinion, Mailed On Mar. 26, 2021, 7 pages.
Takasaka et al., Integrin αvβ8-expressing tumor cells evade host immunity by regulating TGF-β activation in immune cells. JCI Insight. 2018:3(20):e122591. (Year: 2018).
Seed et al., Inhibition of Integrin Avβ8-mediated TGF-β Activation with C6d4 Provides Improved Potency and Selectivity vs. General TGF-β Inhibitors For Cancer Immunotheraphy. Journal for Immuno Therapy of Cancer, (Nov. 2020) vol. 8, No. SUPPL 3. pp. A432-A433. Abstract No. 722 (Year: 2020).
Reszka-Blanco, et al., Inhibition of Integrin αVβ8 in Combination with Low Dose Radiation Induces Antitumor Effect in Advanced Immune Checkpoint Blockade Refractory Tumor Model, The Journal for ImmunoTherapy of Cancer, vol. 9, p. A625, ( 2021).

* cited by examiner

*Primary Examiner* — Maher M Haddad
(74) *Attorney, Agent, or Firm* — Kilpatrick Townsend & Stockton LLP

(57) ABSTRACT

Antibodies that bind to αvβ8 are provided.

10 Claims, 8 Drawing Sheets

Specification includes a Sequence Listing.

FIG. 1

|        | | CDR1 | | CDR2 | | CDR3 | |
|---|---|---|---|---|---|---|---|
| C6D4_Vk | DIVMTQSPSSLAVSAGEKVTMSC | KSSQSLL-NSRTRK---NYLA | WYQQKPGQSPRLLIY | WASTRES | GVPDRFTGSGSGTDFTLTISSVQAEDLAVYYC | KQSYNLLS | FGAGTKLELKA |
| HuC6D4_Vk | EIVMTQSPATLSVSPGERVTMSC | KSSQSLL-NSRSRK---NYLA | WYQQKPGQAPRLLIY | WASTRES | GVPARFSGSGSGTEFTLTISSVQSEDFAVYYC | KQSYNLLS | PGQGTVLEIKR |
| HuC6D4-RGD3_Vk | EIVMTQSPATLSVSPGERVTMSC | KSSQSLLRRGDLGRLKKNALA | WYQQKPGQAPRLLIY | WASTRES | GVPARFSGSGSGTEFTLTISSVQSEDFAVYYC | KQSYNLLS | FGQGTVLEIKR |
| HuC6-TGFβ1RGD_Vk | EIVMTQSPATLSVSPGERVTMSC | KSSQSLLRRGDLATIHGNALA | WYQQKPGQAPRLLIY | WASTRES | GVPARFSGSGSGTEFTLTISSVQSEDFAVYYC | KQSYNLLS | FGQGTVLEIKR |

|        | | CDR1 | | CDR2 | | CDR3 | |
|---|---|---|---|---|---|---|---|
| HuC6D4_Vh | QIQLVQSGAEVKKPGASVKISCKASGY | TFTDYSMH | WVRQAPGQGLEWVA | RINTETGEPTFADDFRG | RFTVLDTSTSTAYLEIRSLRSDDTAVYFCAI | FYYGRDT | WGQGTTLTVSS |
| HuC6D4F12_Vh | QIQLVQSGAEVKKPGASVKISCKASGY | TFTKYSMH | WVRQAPGQGLEWVA | RINTETGEPTFADDFRG | RFTVLDTSTSTAYLEIRSLRSDDTAVYFCAI | FYYGRDT | WGQGTTLTVSS |

|        | | CDR1 | | CDR2 | | CDR3 | |
|---|---|---|---|---|---|---|---|
| HuC6D4_Vk | EIVMTQSPATLSVSPGERVTMSC | KSSQSLLNSRSRKNYLA | WYQQKPGQAPRLLIY | WASTRES | GVPARFSGSGSGTEFTLTISSVQSEDFAVYYC | KQSYNLLS | FGQGTVLEIKR |
| HuC6D4F12_Vk | EIVMTQSPATLSVSPGERVTMSC | KSSQSLLHSRSRKNYLA | WYQQKPGQAPRLLIY | WASTRES | GVPARFSGSGSGTEFTLTISSVQSEDFAVYYC | KQSYNLLS | FGQGTVLEIKR |

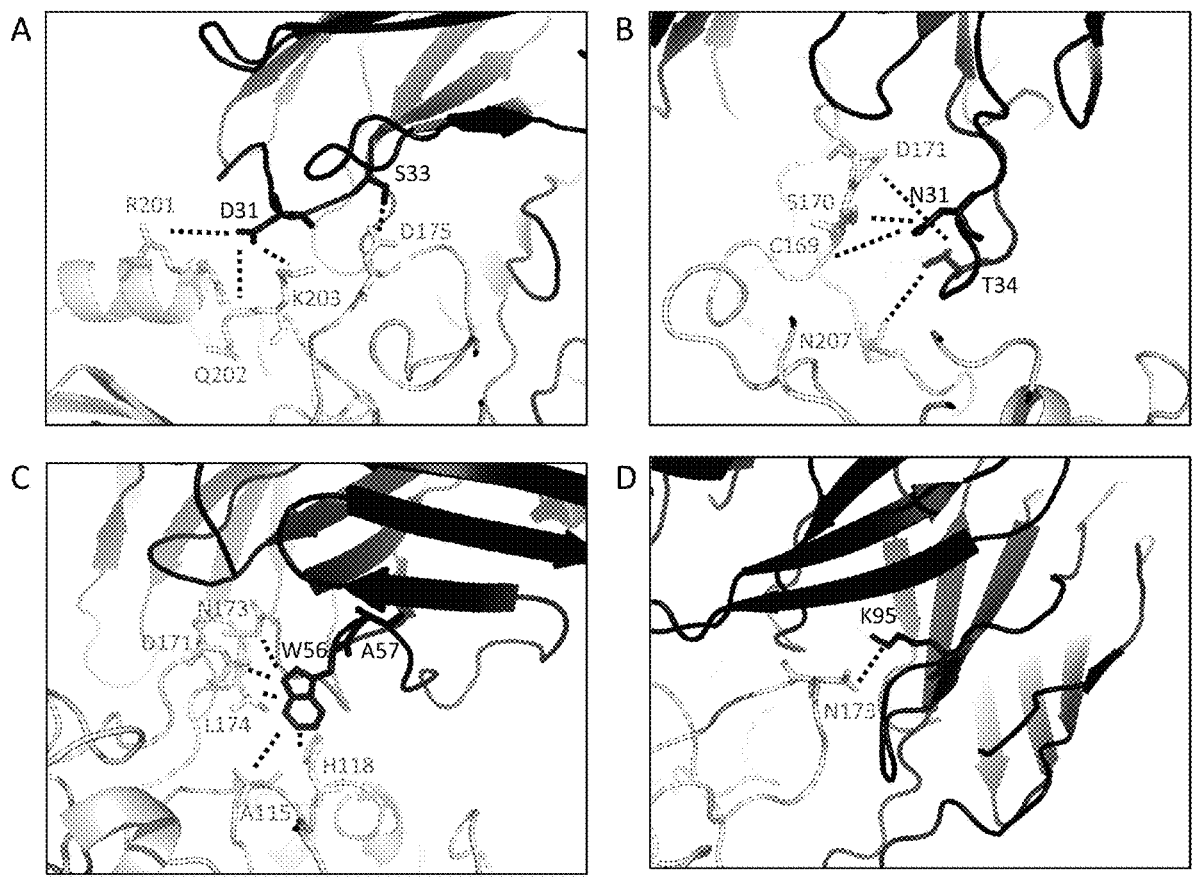
FIG. 2A-D

Fig. 3A-D
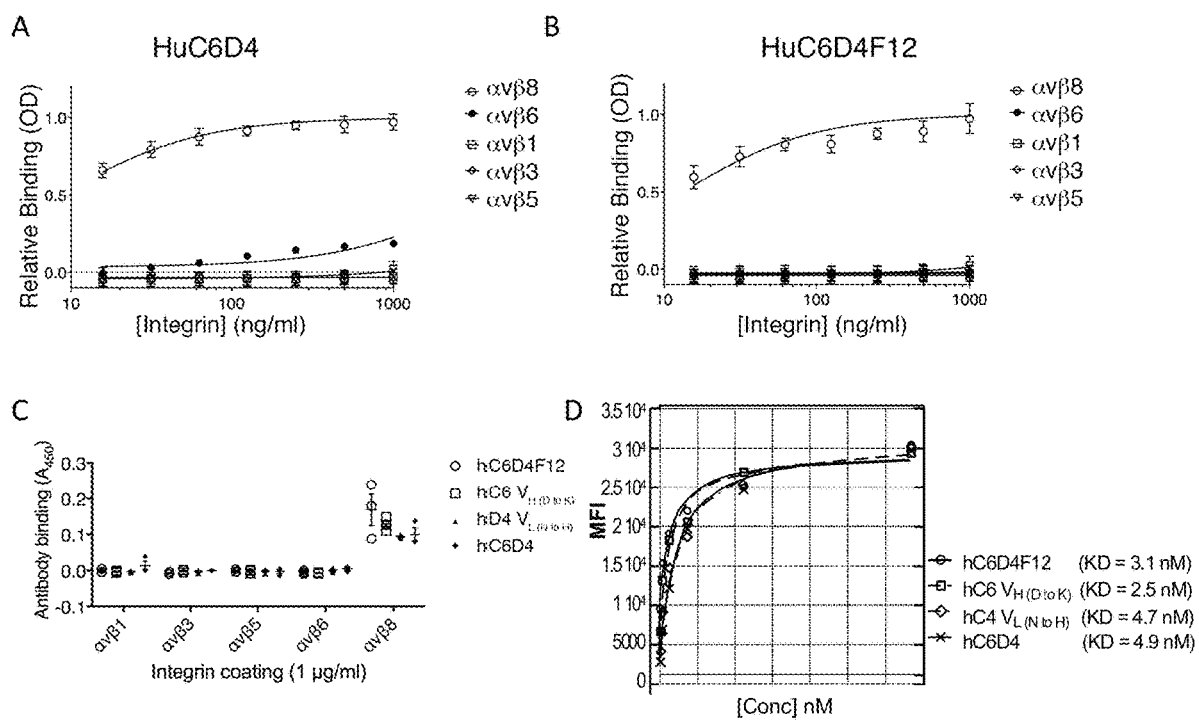

FIG. 4A-B
Inhibition of αvβ8-mediated TGF-β activation
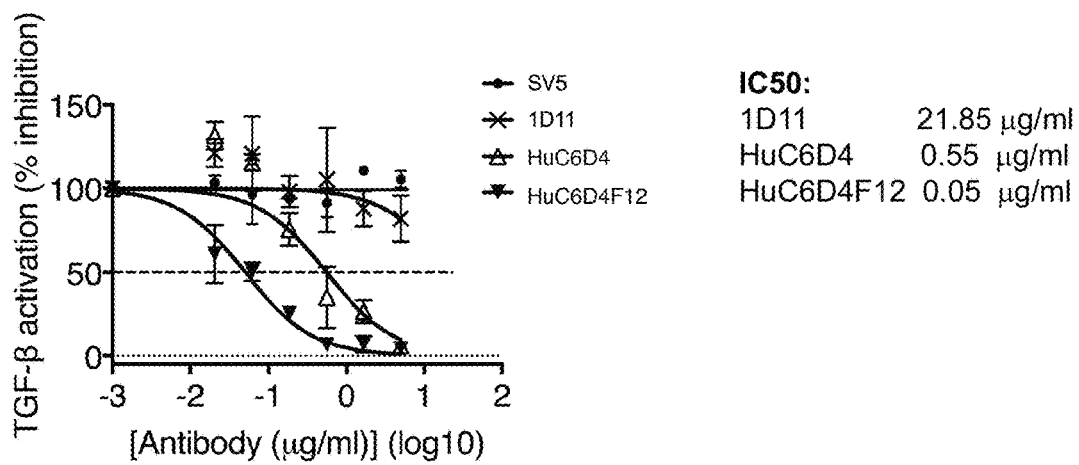
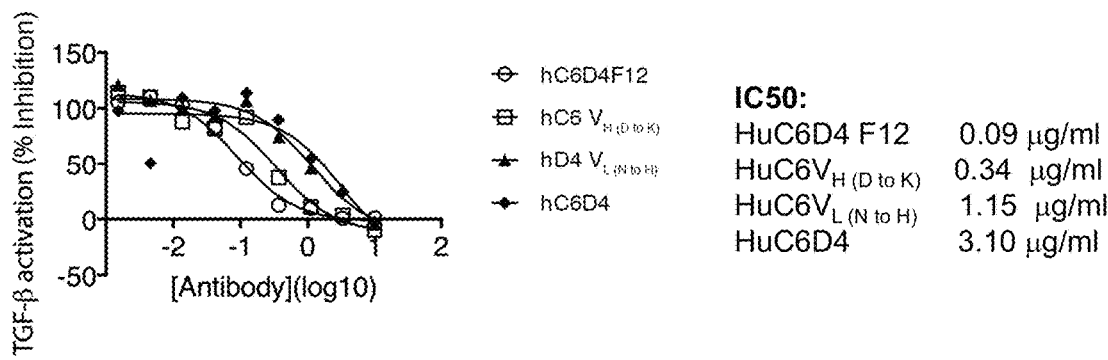

FIG. 7A-C
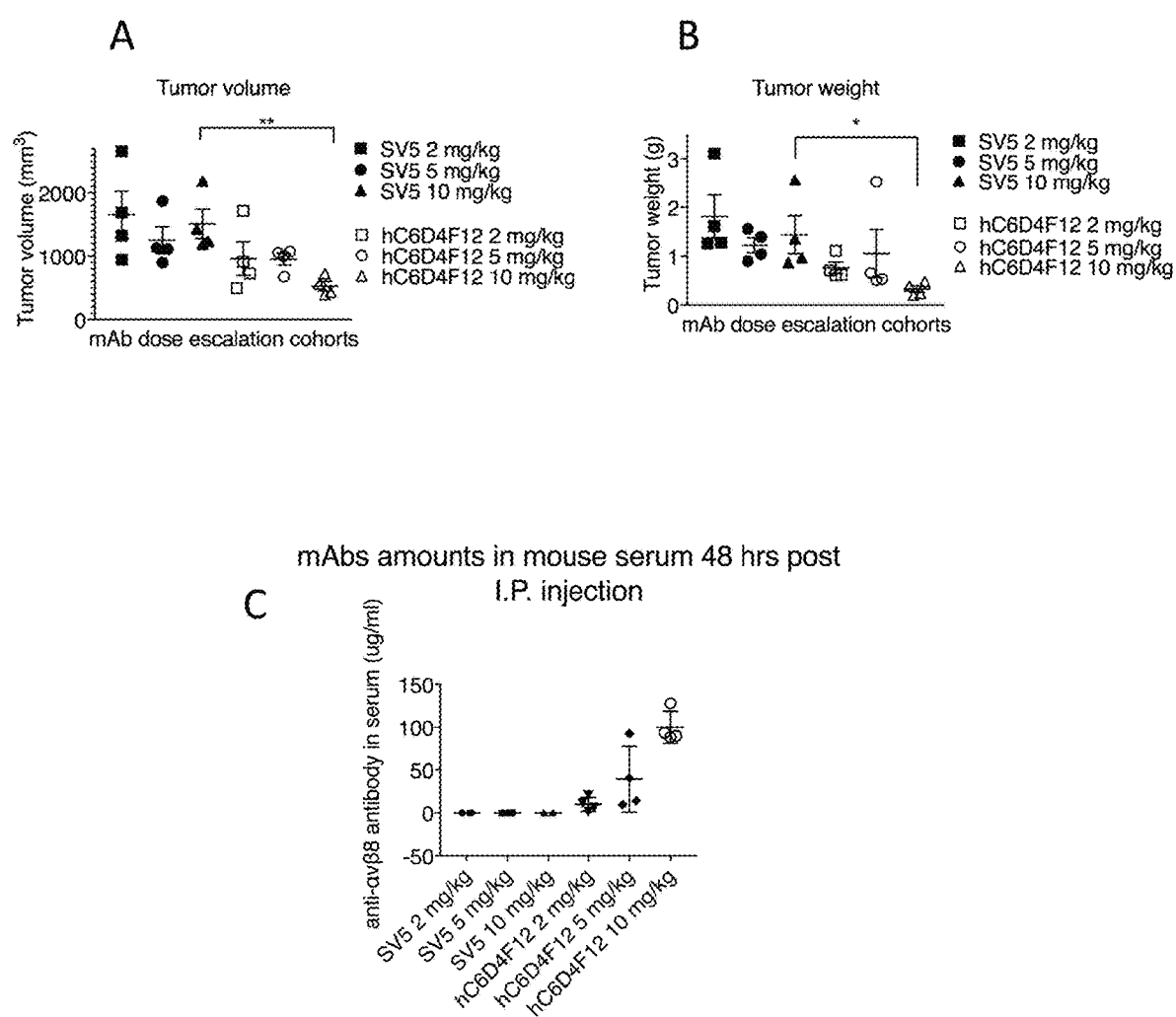

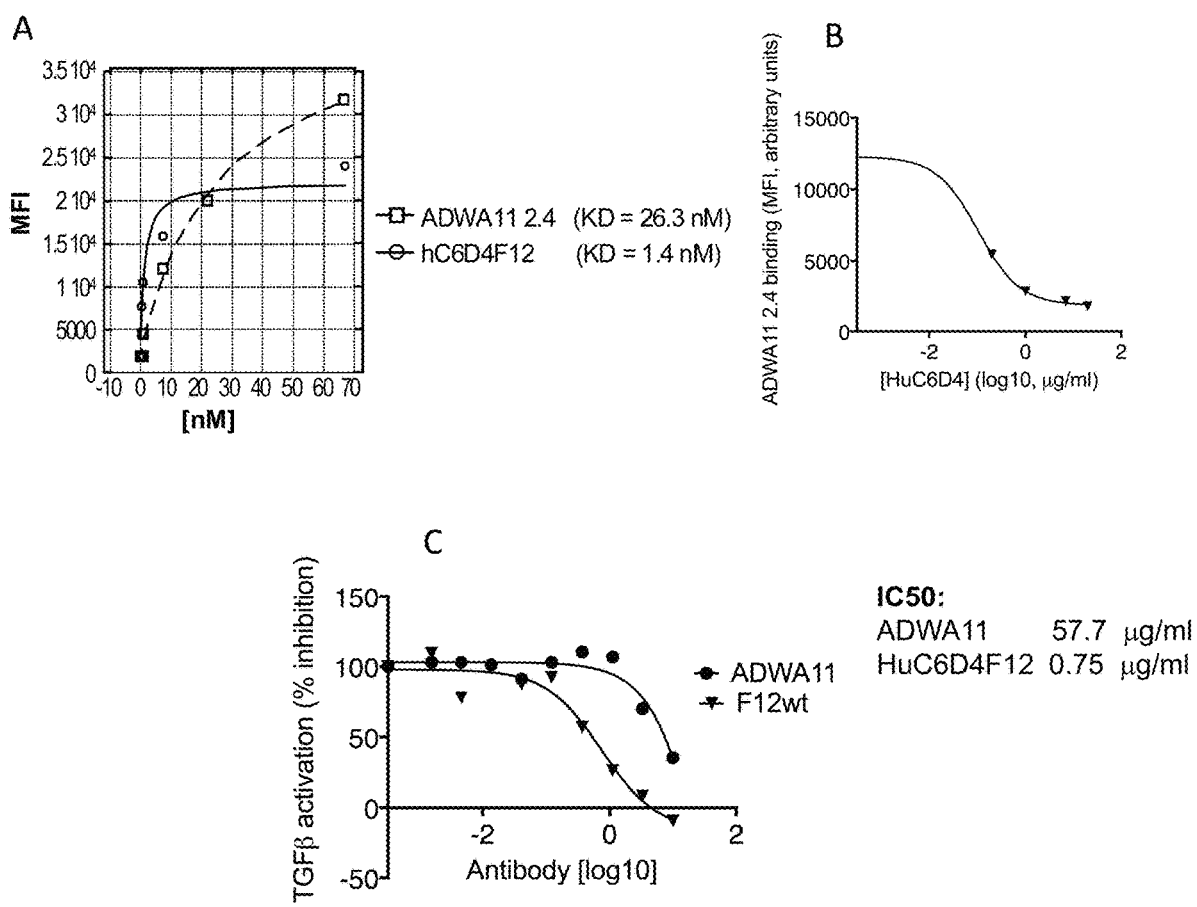
FIG. 8A-C

```
                              SEQUENCE LISTING

Sequence total quantity: 76
SEQ ID NO: 1             moltype = AA  length = 8
FEATURE                  Location/Qualifiers
REGION                   1..8
                         note = Description of sequence: Antibody component
source                   1..8
                         mol_type = protein
                         organism = synthetic construct
SEQUENCE: 1
TFTDYSMH                                                                   8

SEQ ID NO: 2             moltype = AA  length = 8
FEATURE                  Location/Qualifiers
REGION                   1..8
                         note = Description of sequence: Antibody component
source                   1..8
                         mol_type = protein
                         organism = synthetic construct
SEQUENCE: 2
TFTKYSMH                                                                   8

SEQ ID NO: 3             moltype = AA  length = 17
FEATURE                  Location/Qualifiers
REGION                   1..17
                         note = Description of sequence: Antibody component
source                   1..17
                         mol_type = protein
                         organism = synthetic construct
SEQUENCE: 3
RINTETGEPT FADDFRG                                                        17

SEQ ID NO: 4             moltype = AA  length = 7
FEATURE                  Location/Qualifiers
REGION                   1..7
                         note = Description of sequence: Antibody component
VARIANT                  7
                         note = S or T
source                   1..7
                         mol_type = protein
                         organism = synthetic construct
SEQUENCE: 4
FYYGRDX                                                                    7

SEQ ID NO: 5             moltype = AA  length = 17
FEATURE                  Location/Qualifiers
REGION                   1..17
                         note = Description of sequence: Antibody component
source                   1..17
                         mol_type = protein
                         organism = synthetic construct
SEQUENCE: 5
KSSQSLLNSR SRKNYLA                                                        17

SEQ ID NO: 6             moltype = AA  length = 17
FEATURE                  Location/Qualifiers
REGION                   1..17
                         note = Description of sequence: Antibody component
source                   1..17
                         mol_type = protein
                         organism = synthetic construct
```

```
SEQUENCE: 6
KSSQSLLHSR SRKNYLA                                                          17

SEQ ID NO: 7            moltype = AA  length = 7
FEATURE                 Location/Qualifiers
REGION                  1..7
                        note = Description of sequence: Antibody component
source                  1..7
                        mol_type = protein
                        organism = synthetic construct
SEQUENCE: 7
WASTRES                                                                      7

SEQ ID NO: 8            moltype = AA  length = 8
FEATURE                 Location/Qualifiers
REGION                  1..8
                        note = Description of sequence: Antibody component
source                  1..8
                        mol_type = protein
                        organism = synthetic construct
SEQUENCE: 8
KQSYNLLS                                                                     8

SEQ ID NO: 9            moltype = AA  length = 116
FEATURE                 Location/Qualifiers
REGION                  1..116
                        note = Description of sequence: Antibody component
source                  1..116
                        mol_type = protein
                        organism = synthetic construct
SEQUENCE: 9
QIQLVQSGAE VKKPGASVKI SCKASGYTFT KYSMHWVRQA PGQGLEWVAR INTETGEPTF           60
ADDFRGRFTV TLDTSTSTAY LEIRSLRSDD TAVYFCAIFY YGRDTWGQGT TLTVSS              116

SEQ ID NO: 10           moltype = AA  length = 113
FEATURE                 Location/Qualifiers
REGION                  1..113
                        note = Description of sequence: Antibody component
source                  1..113
                        mol_type = protein
                        organism = synthetic construct
SEQUENCE: 10
EIVMTQSPAT LSVSPGERVT MSCKSSQSLL HSRSRKNYLA WYQQKPGQAP RLLIYWASTR           60
ESGVPARFSG SGSGTEFTLT ISSVQSEDFA VYYCKQSYNL LSFGQGTVLE IKR                 113

SEQ ID NO: 11           moltype = AA  length = 21
FEATURE                 Location/Qualifiers
REGION                  1..21
                        note = Description of sequence: Antibody component
source                  1..21
                        mol_type = protein
                        organism = synthetic construct
SEQUENCE: 11
KSSQSLLRRG DLATIHGNAL A                                                     21

SEQ ID NO: 12           moltype = AA  length = 117
FEATURE                 Location/Qualifiers
REGION                  1..117
                        note = Description of sequence: Antibody component
source                  1..117
                        mol_type = protein
                        organism = synthetic construct
SEQUENCE: 12
EIVMTQSPAT LSVSPGERVT MSCKSSQSLL RRGDLATIHG NALAWYQQKP GQAPRLLIYW           60
ASTRESGVPA RFSGSGSGTE FTLTISSVQS EDFAVYYCKQ SYNLLSFGQG TVLEIKR             117

SEQ ID NO: 13           moltype = AA  length = 27
FEATURE                 Location/Qualifiers
REGION                  1..27
                        note = Description of sequence: Antibody component
VARIANT                 1
                        note = Q or E
VARIANT                 5
                        note = L or M
VARIANT                 6
                        note = Q or E
source                  1..27
                        mol_type = protein
                        organism = synthetic construct
```

```
SEQUENCE: 13
XIQLXXSGPE LKKPGETVKI SCKASGY                                            27

SEQ ID NO: 14            moltype = AA  length = 14
FEATURE                  Location/Qualifiers
REGION                   1..14
                         note = Description of sequence: Antibody component
VARIANT                  13
                         note = V or M
source                   1..14
                         mol_type = protein
                         organism = synthetic construct
SEQUENCE: 14
WVKQAPGKGL KWXA                                                          14

SEQ ID NO: 15            moltype = AA  length = 23
FEATURE                  Location/Qualifiers
REGION                   1..23
                         note = Description of sequence: Antibody component
VARIANT                  1
                         note = D or E
VARIANT                  5
                         note = T or S
VARIANT                  14
                         note = S or P
VARIANT                  18
                         note = K or N
VARIANT                  21
                         note = M or V
source                   1..23
                         mol_type = protein
                         organism = synthetic construct
SEQUENCE: 15
XIVMXQSPSS LAVXAGEXVT XSC                                                23

SEQ ID NO: 16            moltype = AA  length = 15
FEATURE                  Location/Qualifiers
REGION                   1..15
                         note = Description of sequence: Antibody component
VARIANT                  11
                         note = R or K
source                   1..15
                         mol_type = protein
                         organism = synthetic construct
SEQUENCE: 16
WYQQKPGQSP XLLIY                                                         15

SEQ ID NO: 17            moltype = AA  length = 32
FEATURE                  Location/Qualifiers
REGION                   1..32
                         note = Description of sequence: Antibody component
VARIANT                  4
                         note = V or F
source                   1..32
                         mol_type = protein
                         organism = synthetic construct
SEQUENCE: 17
RFAXSLETSA STAYLQINNL KNEDTATYFC AI                                      32

SEQ ID NO: 18            moltype = AA  length = 11
FEATURE                  Location/Qualifiers
REGION                   1..11
                         note = Description of sequence: Antibody component
VARIANT                  7
                         note = L or V
source                   1..11
                         mol_type = protein
                         organism = synthetic construct
SEQUENCE: 18
WGQGTTXTVS S                                                             11

SEQ ID NO: 19            moltype = AA  length = 32
FEATURE                  Location/Qualifiers
REGION                   1..32
                         note = Description of sequence: Antibody component
VARIANT                  31
                         note = Y or F
source                   1..32
                         mol_type = protein
```

```
                              -continued
                         organism = synthetic construct
SEQUENCE: 19
GVPDRFTGSG SGTDFTLTIS SVQAEDLAVY XC                               32

SEQ ID NO: 20            moltype = AA   length = 10
FEATURE                  Location/Qualifiers
REGION                   1..10
                         note = Description of sequence: Antibody component
VARIANT                  6
                         note = K or R
VARIANT                  9
                         note = L or I
source                   1..10
                         mol_type = protein
                         organism = synthetic construct
SEQUENCE: 20
FGAGTXLEXK                                                        10

SEQ ID NO: 21            moltype = AA   length = 30
FEATURE                  Location/Qualifiers
REGION                   1..30
                         note = Description of sequence: Antibody component
VARIANT                  9
                         note = P or A
VARIANT                  10
                         note = E or K
VARIANT                  11
                         note = L or V
VARIANT                  16
                         note = E or A
VARIANT                  17
                         note = T or S
source                   1..30
                         mol_type = protein
                         organism = synthetic construct
SEQUENCE: 21
QIQLVQSGXX XKKPGXXVKI SCKASGYTFT                                  30

SEQ ID NO: 22            moltype = AA   length = 14
FEATURE                  Location/Qualifiers
REGION                   1..14
                         note = Description of sequence: Antibody component
VARIANT                  3
                         note = K or R
VARIANT                  8
                         note = K or Q
VARIANT                  11
                         note = K or E
source                   1..14
                         mol_type = protein
                         organism = synthetic construct
SEQUENCE: 22
WVXQAPGXGL XWVA                                                   14

SEQ ID NO: 23            moltype = AA   length = 23
FEATURE                  Location/Qualifiers
REGION                   1..23
                         note = Description of sequence: Antibody component
VARIANT                  1
                         note = D or E
VARIANT                  7
                         note = S or T
VARIANT                  9
                         note = S, A or V
VARIANT                  10
                         note = S or T
VARIANT                  12
                         note = A or S
VARIANT                  15
                         note = A or P
VARIANT                  18
                         note = K, R or I
source                   1..23
                         mol_type = protein
                         organism = synthetic construct
SEQUENCE: 23
XIVMTQXPXX LXVSXGEXVT MSC                                         23

SEQ ID NO: 24            moltype = AA   length = 15
```

```
FEATURE                  Location/Qualifiers
REGION                   1..15
                         note = Description of sequence: Antibody component
VARIANT                  9
                         note = S or A
source                   1..15
                         mol_type = protein
                         organism = synthetic construct
SEQUENCE: 24
WYQQKPGQXP RLLIY                                                          15

SEQ ID NO: 25            moltype = AA  length = 32
FEATURE                  Location/Qualifiers
REGION                   1..32
                         note = Description of sequence: Antibody component
VARIANT                  3
                         note = A, T or S
VARIANT                  5
                         note = S or T
VARIANT                  7
                         note = E or D
VARIANT                  10
                         note = A or T
VARIANT                  16
                         note = Q or E
VARIANT                  18
                         note = N, R or T
VARIANT                  19
                         note = N or S
VARIANT                  21
                         note = K or R
VARIANT                  22
                         note = N or S
VARIANT                  23
                         note = E or D
VARIANT                  27
                         note = T or V
source                   1..32
                         mol_type = protein
                         organism = synthetic construct
SEQUENCE: 25
RFXVXLXTSX STAYLXIXXL XXXDTAXYFC AI                                       32

SEQ ID NO: 26            moltype = AA  length = 32
FEATURE                  Location/Qualifiers
REGION                   1..32
                         note = Description of sequence: Antibody component
VARIANT                  1
                         note = G or D
VARIANT                  4
                         note = D or A
VARIANT                  7
                         note = T or S
VARIANT                  14
                         note = D or E
VARIANT                  24
                         note = A or S
VARIANT                  27
                         note = L or F
source                   1..32
                         mol_type = protein
                         organism = synthetic construct
SEQUENCE: 26
XVPXRFXGSG SGTXFTLTIS SVQXEDXAVY YC                                       32

SEQ ID NO: 27            moltype = AA  length = 11
FEATURE                  Location/Qualifiers
REGION                   1..11
                         note = Description of sequence: Antibody component
VARIANT                  6
                         note = T or A
source                   1..11
                         mol_type = protein
                         organism = synthetic construct
SEQUENCE: 27
WGQGTXLTVS S                                                              11

SEQ ID NO: 28            moltype = AA  length = 11
FEATURE                  Location/Qualifiers
```

```
REGION            1..11
                  note = Description of sequence: Antibody component
VARIANT           3
                  note = A or Q
VARIANT           6
                  note = K or V
VARIANT           9
                  note = L or I
source            1..11
                  mol_type = protein
                  organism = synthetic construct
SEQUENCE: 28
FGXGTXLEXK R                                                                      11

SEQ ID NO: 29     moltype = AA   length = 30
FEATURE           Location/Qualifiers
REGION            1..30
                  note = Description of sequence: Antibody component
VARIANT           5
                  note = V or L
VARIANT           9
                  note = P or A
VARIANT           10
                  note = E or K
VARIANT           11
                  note = L or V
VARIANT           16
                  note = E or A
VARIANT           17
                  note = T or S
source            1..30
                  mol_type = protein
                  organism = synthetic construct
SEQUENCE: 29
QIQLXQSGXX XKKPGXXVKI SCKASGYTFT                                                  30

SEQ ID NO: 30     moltype = AA   length = 14
FEATURE           Location/Qualifiers
REGION            1..14
                  note = Description of sequence: Antibody component
VARIANT           3
                  note = K or R
VARIANT           8
                  note = K or Q
VARIANT           11
                  note = K or E
VARIANT           13
                  note = V or M
VARIANT           14
                  note = A or G
source            1..14
                  mol_type = protein
                  organism = synthetic construct
SEQUENCE: 30
WVXQAPGXGL XWXX                                                                   14

SEQ ID NO: 31     moltype = AA   length = 23
FEATURE           Location/Qualifiers
REGION            1..23
                  note = Description of sequence: Antibody component
VARIANT           1
                  note = D or E
VARIANT           5
                  note = T or S
VARIANT           7
                  note = S or T
VARIANT           9
                  note = S, A or V
VARIANT           10
                  note = S or T
VARIANT           12
                  note = A or S
VARIANT           15
                  note = A or P
VARIANT           18
                  note = K, R or I
source            1..23
                  mol_type = protein
                  organism = synthetic construct
```

```
SEQUENCE: 31
XIVMXQXPXX LXVSXGEXVT MSC                                               23

SEQ ID NO: 32          moltype = AA  length = 15
FEATURE                Location/Qualifiers
REGION                 1..15
                       note = Description of sequence: Antibody component
VARIANT                9
                       note = S or A
source                 1..15
                       mol_type = protein
                       organism = synthetic construct
SEQUENCE: 32
WYQQKPGQXP RLLIY                                                        15

SEQ ID NO: 33          moltype = AA  length = 32
FEATURE                Location/Qualifiers
REGION                 1..32
                       note = Description of sequence: Antibody component
VARIANT                3
                       note = A, T or S
VARIANT                4
                       note = V or F
VARIANT                5
                       note = S or T
VARIANT                7
                       note = E or D
VARIANT                10
                       note = A or T
VARIANT                11
                       note = S or T
VARIANT                14
                       note = Y or N
VARIANT                15
                       note = L or T
VARIANT                16
                       note = Q or E
VARIANT                18
                       note = N, R or I
VARIANT                19
                       note = N or S
VARIANT                21
                       note = K or R
VARIANT                22
                       note = N or S
VARIANT                23
                       note = E or D
VARIANT                27
                       note = T, V or K
source                 1..32
                       mol_type = protein
                       organism = synthetic construct
SEQUENCE: 33
RFXXXLXTSX XTAXXXIXXL XXXDTAXYFC AI                                     32

SEQ ID NO: 34          moltype = AA  length = 32
FEATURE                Location/Qualifiers
REGION                 1..32
                       note = Description of sequence: Antibody component
VARIANT                1
                       note = G or D
VARIANT                4
                       note = D or A
VARIANT                7
                       note = T or S
VARIANT                14
                       note = D or E
VARIANT                24
                       note = A, S or D
VARIANT                27
                       note = L or F
source                 1..32
                       mol_type = protein
                       organism = synthetic construct
SEQUENCE: 34
XVPXRFXGSG SGTXFTLTIS SVQXEDXAVY YC                                     32

SEQ ID NO: 35          moltype = AA  length = 11
FEATURE                Location/Qualifiers
```

```
REGION                  1..11
                        note = Description of sequence: Antibody component
VARIANT                 6
                        note = T or A
source                  1..11
                        mol_type = protein
                        organism = synthetic construct
SEQUENCE: 35
WGQGTXLTVS S                                                              11

SEQ ID NO: 36           moltype = AA   length = 11
FEATURE                 Location/Qualifiers
REGION                  1..11
                        note = Description of sequence: Antibody component
VARIANT                 3
                        note = A or Q
VARIANT                 6
                        note = K or V
VARIANT                 9
                        note = I or L
source                  1..11
                        mol_type = protein
                        organism = synthetic construct
SEQUENCE: 36
FGXGTXLEXK R                                                              11

SEQ ID NO: 37           moltype = AA   length = 116
FEATURE                 Location/Qualifiers
REGION                  1..116
                        note = Description of sequence: Antibody component
source                  1..116
                        mol_type = protein
                        organism = synthetic construct
SEQUENCE: 37
QIQLVQSGAE VKKPGASVKI SCKASGYTFT DYSMHWVRQA PGQGLEWVAR INTETGEPTF          60
ADDFRGRFTV TLDTSTSTAY LEIRSLRSDD TAVYFCAIFY YGRDTWGQGT TLTVSS             116

SEQ ID NO: 38           moltype = AA   length = 7
FEATURE                 Location/Qualifiers
REGION                  1..7
                        note = Description of sequence: Antibody component
source                  1..7
                        mol_type = protein
                        organism = synthetic construct
SEQUENCE: 38
FYYGRDT                                                                    7

SEQ ID NO: 39           moltype = AA   length = 117
FEATURE                 Location/Qualifiers
REGION                  1..117
                        note = Description of sequence: Antibody component
source                  1..117
                        mol_type = protein
                        organism = synthetic construct
SEQUENCE: 39
EIVMTQSPAT LSVSPGERVT MSCKSSQSLL GRGDLGRLKK NALAWYQQKP GQAPRLLIYW          60
ASTRESGVPA RFSGSGSGTE FTLTISSVQS EDFAVYYCKQ SYNLLSFGQG TVLEIKR            117

SEQ ID NO: 40           moltype = AA   length = 21
FEATURE                 Location/Qualifiers
REGION                  1..21
                        note = Description of sequence: Antibody component
source                  1..21
                        mol_type = protein
                        organism = synthetic construct
SEQUENCE: 40
KSSQSLLGRG DLGRLKKNAL A                                                   21

SEQ ID NO: 41           moltype = AA   length = 17
FEATURE                 Location/Qualifiers
REGION                  1..17
                        note = Description of sequence: Antibody component
source                  1..17
                        mol_type = protein
                        organism = synthetic construct
SEQUENCE: 41
KSSQSLLNSR SRKNYLA                                                        17

SEQ ID NO: 42           moltype = AA   length = 19
```

```
FEATURE              Location/Qualifiers
REGION               1..19
                     note = Description of sequence: Antibody component
source               1..19
                     mol_type = protein
                     organism = synthetic construct
SEQUENCE: 42
KSSQSLLNSG RGDLGNALA                                                   19

SEQ ID NO: 43        moltype = AA  length = 25
FEATURE              Location/Qualifiers
REGION               1..25
                     note = Description of sequence: Antibody component
source               1..25
                     mol_type = protein
                     organism = synthetic construct
SEQUENCE: 43
KSSQSLLGRG DLGRLKKQKD HNALA                                            25

SEQ ID NO: 44        moltype = AA  length = 24
FEATURE              Location/Qualifiers
REGION               1..24
                     note = Description of sequence: Antibody component
source               1..24
                     mol_type = protein
                     organism = synthetic construct
SEQUENCE: 44
KSSQSLLGRG DLGRLKKQKD NALA                                             24

SEQ ID NO: 45        moltype = AA  length = 23
FEATURE              Location/Qualifiers
REGION               1..23
                     note = Description of sequence: Antibody component
source               1..23
                     mol_type = protein
                     organism = synthetic construct
SEQUENCE: 45
KSSQSLLGRG DLGRLKKQKN ALA                                              23

SEQ ID NO: 46        moltype = AA  length = 22
FEATURE              Location/Qualifiers
REGION               1..22
                     note = Description of sequence: Antibody component
source               1..22
                     mol_type = protein
                     organism = synthetic construct
SEQUENCE: 46
KSSQSLLGRG DLGRLKKQNA LA                                               22

SEQ ID NO: 47        moltype = AA  length = 21
FEATURE              Location/Qualifiers
REGION               1..21
                     note = Description of sequence: Antibody component
source               1..21
                     mol_type = protein
                     organism = synthetic construct
SEQUENCE: 47
KSSQSLLGRG DLGRLKKNAL A                                                21

SEQ ID NO: 48        moltype = AA  length = 20
FEATURE              Location/Qualifiers
REGION               1..20
                     note = Description of sequence: Antibody component
source               1..20
                     mol_type = protein
                     organism = synthetic construct
SEQUENCE: 48
KSSQSLLGRG DLGRLKNALA                                                  20

SEQ ID NO: 49        moltype = AA  length = 19
FEATURE              Location/Qualifiers
REGION               1..19
                     note = Description of sequence: Antibody component
source               1..19
                     mol_type = protein
                     organism = synthetic construct
SEQUENCE: 49
KSSQSLLGRG DLGRLNALA                                                   19
```

```
SEQ ID NO: 50          moltype = AA   length = 18
FEATURE                Location/Qualifiers
REGION                 1..18
                       note = Description of sequence: Antibody component
source                 1..18
                       mol_type = protein
                       organism = synthetic construct
SEQUENCE: 50
KSSQSLLGRG DLGRNALA                                                      18

SEQ ID NO: 51          moltype = AA   length = 17
FEATURE                Location/Qualifiers
REGION                 1..17
                       note = Description of sequence: Antibody component
source                 1..17
                       mol_type = protein
                       organism = synthetic construct
SEQUENCE: 51
KSSQSLLGRG DLGNALA                                                       17

SEQ ID NO: 52          moltype = AA   length = 22
FEATURE                Location/Qualifiers
REGION                 1..22
                       note = Description of sequence: Antibody component
source                 1..22
                       mol_type = protein
                       organism = synthetic construct
SEQUENCE: 52
KSSQSLLGRG DLGRLKKQKD HH                                                 22

SEQ ID NO: 53          moltype = AA   length = 21
FEATURE                Location/Qualifiers
REGION                 1..21
                       note = Description of sequence: Antibody component
source                 1..21
                       mol_type = protein
                       organism = synthetic construct
SEQUENCE: 53
KSSQSLLGRG DLGRLKKQKD H                                                  21

SEQ ID NO: 54          moltype = AA   length = 20
FEATURE                Location/Qualifiers
REGION                 1..20
                       note = Description of sequence: Antibody component
source                 1..20
                       mol_type = protein
                       organism = synthetic construct
SEQUENCE: 54
KSSQSLLGRG DLGRLKKQKD                                                    20

SEQ ID NO: 55          moltype = AA   length = 19
FEATURE                Location/Qualifiers
REGION                 1..19
                       note = Description of sequence: Antibody component
source                 1..19
                       mol_type = protein
                       organism = synthetic construct
SEQUENCE: 55
KSSQSLLGRG DLGRLKKQK                                                     19

SEQ ID NO: 56          moltype = AA   length = 18
FEATURE                Location/Qualifiers
REGION                 1..18
                       note = Description of sequence: Antibody component
source                 1..18
                       mol_type = protein
                       organism = synthetic construct
SEQUENCE: 56
KSSQSLLGRG DLGRLKKQ                                                      18

SEQ ID NO: 57          moltype = AA   length = 17
FEATURE                Location/Qualifiers
REGION                 1..17
                       note = Description of sequence: Antibody component
source                 1..17
                       mol_type = protein
                       organism = synthetic construct
SEQUENCE: 57
KSSQSLLGRG DLGRLKK                                                       17
```

```
SEQ ID NO: 58          moltype = AA  length = 16
FEATURE                Location/Qualifiers
REGION                 1..16
                       note = Description of sequence: Antibody component
source                 1..16
                       mol_type = protein
                       organism = synthetic construct
SEQUENCE: 58
KSSQSLLGRG DLGRLK                                                    16

SEQ ID NO: 59          moltype = AA  length = 15
FEATURE                Location/Qualifiers
REGION                 1..15
                       note = Description of sequence: Antibody component
source                 1..15
                       mol_type = protein
                       organism = synthetic construct
SEQUENCE: 59
KSSQSLLGRG DLGRL                                                     15

SEQ ID NO: 60          moltype = AA  length = 4
FEATURE                Location/Qualifiers
REGION                 1..4
                       note = Description of sequence: Antibody component
source                 1..4
                       mol_type = protein
                       organism = synthetic construct
SEQUENCE: 60
RGDL                                                                  4

SEQ ID NO: 61          moltype = AA  length = 10
FEATURE                Location/Qualifiers
REGION                 1..10
                       note = Description of sequence: Antibody component
source                 1..10
                       mol_type = protein
                       organism = synthetic construct
SEQUENCE: 61
GRGDLGRLKK                                                           10

SEQ ID NO: 62          moltype = AA  length = 116
FEATURE                Location/Qualifiers
REGION                 1..116
                       note = Description of sequence: Antibody component
source                 1..116
                       mol_type = protein
                       organism = synthetic construct
SEQUENCE: 62
QIQLVQSGPE LKKPGETVKI SCKASGYTFT DYSMHWVKQA PGKGLKWVAR INTETGEPTF  60
ADDFRGRFAV SLETSASTAY LQINNLKNED TATYFCAIFY YGRDSWGQGT TLTVSS     116

SEQ ID NO: 63          moltype = AA  length = 113
FEATURE                Location/Qualifiers
REGION                 1..113
                       note = Description of sequence: Antibody component
source                 1..113
                       mol_type = protein
                       organism = synthetic construct
SEQUENCE: 63
DIVMTQSPSS LAVSAGEKVT MSCKSSQSLL NSRTRKNYLA WYQQKPGQSP RLLIYWASTR  60
ESGVPDRFTG SGSGTDFTLT ISSVQAEDLA VYYCKQSYNL LSFGAGTKLE LKR         113

SEQ ID NO: 64          moltype = AA  length = 113
FEATURE                Location/Qualifiers
REGION                 1..113
                       note = Description of sequence: Antibody component
source                 1..113
                       mol_type = protein
                       organism = synthetic construct
SEQUENCE: 64
EIVMTQSPAT LSVSPGERVT MSCKSSQSLL NSRSRKNYLA WYQQKPGQAP RLLIYWASTR  60
ESGVPARFSG SGSGTEFTLT ISSVQSEDFA VYYCKQSYNL LSFGQGTVLE IKR         113

SEQ ID NO: 65          moltype = DNA  length = 38
FEATURE                Location/Qualifiers
misc_feature           1..38
                       note = Description of Sequence: Synthetic primer
variation              18
```

```
                         note = a, c, t, g, unknown or other
source                   1..38
                         mol_type = other DNA
                         organism = synthetic construct
SEQUENCE: 65
ggttatacct tcacavanta twctatgcat tgggttag                            38

SEQ ID NO: 66            moltype = DNA   length = 38
FEATURE                  Location/Qualifiers
misc_feature             1..38
                         note = Description of Sequence: Synthetic primer
variation                21
                         note = a, c, t, g, unknown or other
source                   1..38
                         mol_type = other DNA
                         organism = synthetic construct
SEQUENCE: 66
ctaacccaat gcatagwata ntbtgtgaag gtataacc                            38

SEQ ID NO: 67            moltype = DNA   length = 47
FEATURE                  Location/Qualifiers
misc_feature             1..47
                         note = Description of Sequence: Synthetic primer
source                   1..47
                         mol_type = other DNA
                         organism = synthetic construct
SEQUENCE: 67
cacaatcgtt gttamattca agawykagaa agaattattt ggcttgg                  47

SEQ ID NO: 68            moltype = DNA   length = 47
FEATURE                  Location/Qualifiers
misc_feature             1..47
                         note = Description of Sequence: Synthetic primer
source                   1..47
                         mol_type = other DNA
                         organism = synthetic construct
SEQUENCE: 68
ccaagccaaa taattctttc tmrwtcttga atktaacaac gattgtg                  47

SEQ ID NO: 69            moltype = DNA   length = 40
FEATURE                  Location/Qualifiers
misc_feature             1..40
                         note = Description of Sequence: Synthetic primer
variation                18
                         note = a, c, t, g, unknown or other
source                   1..40
                         mol_type = other DNA
                         organism = synthetic construct
SEQUENCE: 69
ccaagattgt taatckanwr ggcatctaca agagaatcag                          40

SEQ ID NO: 70            moltype = DNA   length = 40
FEATURE                  Location/Qualifiers
misc_feature             1..40
                         note = Description of Sequence: Synthetic primer
variation                23
                         note = a, c, t, g, unknown or other
source                   1..40
                         mol_type = other DNA
                         organism = synthetic construct
SEQUENCE: 70
ctgattctct tgtagatgcc ywntmgatta acaatcttgg                          40

SEQ ID NO: 71            moltype = DNA   length = 50
FEATURE                  Location/Qualifiers
misc_feature             1..50
                         note = Description of Sequence: Synthetic primer
variation                24
                         note = a, c, t, g, unknown or other
source                   1..50
                         mol_type = other DNA
                         organism = synthetic construct
SEQUENCE: 71
gatttcgcag tttactattg cmancaatca tacaacttat tatcattcgg               50

SEQ ID NO: 72            moltype = DNA   length = 50
FEATURE                  Location/Qualifiers
misc_feature             1..50
                         note = Description of Sequence: Synthetic primer
```

```
variation               27
                        note = a, c, t, g, unknown or other
source                  1..50
                        mol_type = other DNA
                        organism = synthetic construct
SEQUENCE: 72
ccgaatgata ataagttgta tgattgntkg caatagtaaa ctgcgaaatc               50

SEQ ID NO: 73           moltype = DNA  length = 17
FEATURE                 Location/Qualifiers
misc_feature            1..17
                        note = Description of Sequence: oligonucleotide 5 scFV F
source                  1..17
                        mol_type = other DNA
                        organism = synthetic construct
SEQUENCE: 73
ggtggaggcg gttccgg                                                   17

SEQ ID NO: 74           moltype = DNA  length = 27
FEATURE                 Location/Qualifiers
misc_feature            1..27
                        note = Description of Sequence: oligonucleotide 5 scFV R
source                  1..27
                        mol_type = other DNA
                        organism = synthetic construct
SEQUENCE: 74
caatggtgat ggtgatgatg accgtac                                        27

SEQ ID NO: 75           moltype = AA  length = 10
FEATURE                 Location/Qualifiers
source                  1..10
                        mol_type = protein
                        organism = Homo sapiens
SEQUENCE: 75
RRGDLATIHG                                                           10

SEQ ID NO: 76           moltype = AA  length = 113
FEATURE                 Location/Qualifiers
REGION                  1..113
                        note = Description of sequence: Antibody component
source                  1..113
                        mol_type = protein
                        organism = synthetic construct
SEQUENCE: 76
DIVMTQSPSS LAVSAGEKVT MSCKSSQSLL NSRTRKNYLA WYQQKPGQSP RLLIYWASTR    60
ESGVPDRFTG SGSGTDFTLT ISSVQAEDLA VYYCKQSYNL LSFGAGTKLE LKA          113
```

ANTIBODIES THAT BIND INTEGRIN αvβ8 AND USES THEREOF

CROSS-REFERENCE TO RELATED PATENT APPLICATIONS

The present application is a continuation of U.S. patent application Ser. No. 17/151,009, filed Jan. 15, 2021, which claims benefit of priority to U.S. Provisional Patent Application No. 62/961,625, filed Jan. 15, 2020, and 63/017,868, filed Apr. 30, 2020, which are all incorporated by reference for all purposes.

STATEMENT AS TO RIGHTS TO INVENTIONS MADE UNDER FEDERALLY SPONSORED RESEARCH AND DEVELOPMENT

This invention was made with government support under grants. P41 CA196276, R01 HL113032, R01 HL134183 and U54 HL119893 awarded by The National Institutes of Health. The government has certain rights in the invention.

SEQUENCE LISTING

A Sequence Listing conforming to the rules of WIPO Standard ST.26 is hereby incorporated by reference. Said Sequence Listing has been filed as an electronic document via PatentCenter in ASCII format encoded as XML. The electronic document, created on Mar. 2, 2023, is entitled "081906-1332714-239030US_ST26.xml" and is 136,907 bytes in size.

BACKGROUND OF THE INVENTION

Transforming growth factor β (TGFβ) was originally characterized as an oncogene capable of inducing a transformed phenotype in non-neoplastic cells. A number of TGFβ family members have since been characterized, based on the presence of similar amino acid domains.

Some TGF-β isoforms are expressed ubiquitously in mammals (TGF-β 1-3), but are maintained in an inactive form by non-covalent interaction with a propeptide, the latency associated domain of TGF-β (LAP). For TGFβ to signal, it must be released from its inactive complex by a process called TGFβ activation. The latent TGF complex includes 3 components: the active (mature) TGFβ dimmer, LAP (latency associated peptide) and LTBP (latent TGFβ binding protein). LAP is a dimer, linked by a disulfide bond, that represents the N-terminal end of the TGFβ precursor protein. The mature TGFβ protein represents the C terminal end (about kD) of the precursor. The bond between the TGFβs and LAP is proteolytically cleaved within the Golgi, but the TGF-β propeptide remains bound to TGFβ by non-covalent interactions. The complex of TGFβ and LAP is called the small latent complex (SLC). It is the association of LAP and TGFβ that confers latency. LAP-TGFβ binding is reversible and the isolated purified components can recombine to form an inactive SLC. Both the SLC and the larger complex are referred to herein as latent TGFβ, as both are inactive.

In general, integrins are adhesion molecules and mediate the attachment of cells to extracellular matrix proteins. Integrin αvβ8 binds to the LAP of TGF-β and mediates the activation of TGF-β1 and 3 (Mu et al. (2002) *J. Cell Biol.* 159:493). Integrin αvβ8-mediated activation of TGF-β is required for in vivo activation of TGF-β (i.e., release of the mature TGF-β polypeptide), thus αvβ8 is a gatekeeper of TGF-β function. Integrin αvβ8 is expressed in normal epithelia (e.g., airway epithelia), mesenchymal cells, and neuronal tissues.

The integrin β8 (Itgb8) has been associated with forkhead box P3 (Foxp3)-positive T cells and T-regulatory-specific epigenetic remodeling. See, e.g., Vandenbon, et al., *Proc. Natl. Acad. Sci. USA* vol. 113 no. 17 pp. E2393-E2402 (2016). FoxP3 is a transcription factor involved in the development of T-regulatory (Treg) cells. Human and mouse effector Treg cells express functional TGF-β-activating integrin αvβ8. See, Worthington, *Immunity* Volume 42, Issue 5, pp. 903-915 (May 2015). Treg cell integrin αvβ8-mediated TGF-β activation is not needed for T cell homeostasis and integrin αvβ8 expression by Treg cells suppresses active inflammation.

BRIEF SUMMARY OF THE INVENTION

Antibodies that bind to αvβ8 are provided as described herein. In some embodiments, the disclosure provides an antibody that specifically binds human αvβ8, wherein the antibody comprises:
a heavy chain complementary determining region (HCDR) 1 comprising TFTDYSMH (SEQ ID NO:1) or TFTKYSMH (SEQ ID NO:2);
a HCDR 2 comprising RINTETGEPTFADDFRG (SEQ ID NO:3);
a HCDR 3 comprising FYYGRD(S/T) (SEQ ID NO:4);
a light chain complementary determining region (LCDR) 1 comprising KSSQSLLNSRSRKNYLA (SEQ ID NO:5) or KSSQSLLHSRSRKNYLA (SEQ ID NO:6);
a LCDR2 comprising WASTRES (SEQ ID NO:7); and
a LCDR3 comprising KQSYNLLS (SEQ ID NO:8), wherein the antibody comprises one or none of SEQ ID NO:1 and SEQ ID NO:5, but not both of SEQ ID NO:1 and SEQ ID NO:5.

In some embodiments, the HCDR1 comprises SEQ ID NO:2 and the LCDR1 comprises SEQ ID NO:6. In some embodiments, the HCDR1 comprises SEQ ID NO:1 and the LCDR1 comprises SEQ ID NO:6. In some embodiments, the HCDR1 comprises SEQ ID NO:2 and the LCDR1 comprises SEQ ID NO:5.

In some embodiments, the antibody comprises a heavy chain variable region comprising SEQ ID NO:9. In some embodiments, the antibody comprises a light chain variable region comprising SEQ ID NO: 10. In some embodiments, the antibody comprises a light chain variable region comprising SEQ ID NO:39. In some embodiments, the antibody comprises a heavy chain variable region comprising SEQ ID NO:9 and a light chain variable region comprising SEQ ID NO: 10. In some embodiments, the antibody comprises a heavy chain variable region comprising SEQ ID NO:9 and a light chain variable region comprising SEQ ID NO:39.

In some embodiments, the antibody is humanized.

In some embodiments, the antibody is linked to a detectable label.

Also provided are antibodies that bind human αvβ8 and αvβ6. In some embodiments, the antibody comprises:
a heavy chain complementary determining region (HCDR) 1 comprising TFTDYSMH (SEQ ID NO:1) or TFTKYSMH (SEQ ID NO:2);
a HCDR 2 comprising RINTETGEPTFADDFRG (SEQ ID NO:3);
a HCDR 3 comprising FYYGRD(S/T) (SEQ ID NO:4);
a light chain complementary determining region (LCDR) 1 comprising KSSQSLLRRGDLATIHGNALA (SEQ ID NO:11);
a LCDR2 comprising WASTRES (SEQ ID NO:7); and
a LCDR3 comprising KQSYNLLS (SEQ ID NO:8).

In some embodiments, the antibody comprises a heavy chain variable region comprising SEQ ID NO:9 or SEQ ID NO:37. In some embodiments, the antibody comprises a light chain variable region comprising SEQ ID NO:12. In some embodiments, the antibody comprises a heavy chain variable region comprising SEQ ID NO:9 or SEQ ID NO:37 and a light chain variable region comprising SEQ ID NO:12.

In some embodiments, the antibody is humanized.

In some embodiments, the antibody is linked to a detectable label.

Also provided are antibodies that bind human αvβ8 and αvβ6, wherein the antibody comprises:

a heavy chain complementary determining region (HCDR) 1 comprising TFTKYSMH (SEQ ID NO:2);

a HCDR 2 comprising RINTETGEPTFADDFRG (SEQ ID NO:3);

a HCDR 3 comprising FYYGRD(S/T) (SEQ ID NO:4);

a light chain complementary determining region (LCDR) 1 comprising a sequence selected from the group consisting of SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, and SEQ ID NO:59;

a LCDR2 comprising WASTRES (SEQ ID NO:7); and a LCDR3 comprising KQSYNLLS (SEQ ID NO:8).

In some embodiments, the HCDR1 comprises SEQ ID NO:2 and the LCDR1 comprises SEQ ID NO:40.

In some embodiments, the antibody comprises a heavy chain variable region comprising SEQ ID NO:9. In some embodiments, the antibody comprises a light chain variable region comprising SEQ ID NO:39. In some embodiments, the antibody comprises both a heavy chain variable region comprising SEQ ID NO:9 and a light chain variable region comprising SEQ ID NO:39.

In some embodiments, the antibody is humanized. In some embodiments, the antibody is linked to a detectable label.

Also provided is a method of enhancing an immune response to cancer in a human individual, the method comprising administering a sufficient amount of an antibody as described above or elsewhere herein to the individual, thereby enhancing an immune response to the cancer. In some embodiments, the cancer is lung cancer. In some embodiments, the cancer is a metastatic cancer. In some embodiments, the cancer is a primary cancer.

Also provided is a method of enhancing an immune response to a viral infection in a human individual, the method comprising administering a sufficient amount of an antibody as described above or elsewhere herein to the individual, thereby enhancing an immune response to the viral infection. In some embodiments, the viral infection is a hepatitis infection. In some embodiments, the viral infection is a hepatitis B infection.

Also provided is a pharmaceutical composition comprising an antibody as described above or elsewhere herein in a pharmaceutically acceptable excipient.

Also provided is a method of detecting the presence, absence, or quantity of human in a sample, the method comprising, contacting an antibody as described above or elsewhere herein to the sample, and detecting or quantifying binding of the antibody to the sample.

BRIEF DESCRIPTION OF THE DRAWINGS

FIG. 1 depicts sequence alignments of antibody variable regions; heavy and light chains (Vh and Vk, respectively), with underlined amino acids indicating the mutations or substituted loops. The top portion of the figure depicts changes to antibody C6D4 to form C6-TGFβ1RGD Vk. The bottom portion of the figure depicts heavy and light chain changes to form antibody HuC6D4F12, which has improved binding characteristics compared to C6D4. FIG. 1 discloses SEQ ID NOS 76, 64, 39, 12, 37, 9, 64, and 10, respectively, in order of appearance.

FIG. 2A-D depicts rational design of select potential mutants to improve or create binding interactions between C6D4 and αvβ8 (αvβ8 in grey, C6D4 in black, potential mutant positions in C6D4 in black sticks, potential new interacting residues in β8 in grey sticks). The dashed lines represent potential new or strengthened interactions. A) CDR1 Vh; D31 which is mutated to K in huC6D4F12 is indicated. B) CDR1 Vk; N31 which is mutated to H in huC6D4F12 is indicated. C) CDR2 Vk D) CDR3 Vk.

FIG. 3A-D. Depicts that HuC6D4F12 is highly specific for αvβ8. The specificity of HuC6D4 (3A) for the 5 αv-integrins was compared with HuC6D4F12 (3B) in an ELISA assay. ELISA plates were coated with antibodies (2 μg/ml), washed, blocked with BSA, and then recombinant integrins were added at the indicated concentrations. After a brief incubation at RT, wells were washed and bound integrin detected with biotin conjugated anti-αv (8B8-biotin, 1 μg/ml) followed by Streptavidin-HRP. FIG. 3C shows that when the heavy chain with the C6 VH1 (D to K) mutation is expressed with Light Chain D4, or the Light chain D4 VL1 (N to H) mutation is expressed with heavy chain C6, the specificity of the resultant antibodies is not affected, as no binding to integrins αvβ1, αvβ3, αvβ5 or αvβ6 is seen. FIG. 3D shows the binding of antibodies to the human Ovarian Carcinoma line OVCAR3 with KD in legend (KaleidaGraph). Antibodies were incubated at the indicated concentrations for 15 min at 4° C. and after washing detected with anti-mouse-PE.

FIG. 4A-B shows HuC6D4F12 is more efficient in blocking TGF-β activation than HuC6D4 TGF-β reporter cells (TMLC) expressing L-TGF-β1/GARP (15,000 cells) on their cell surface were applied to wells coated with recombinant αvβ8 (0.5 mg/ml coating concentration). Humanized C6D4, HuC6D4F12, anti-pan TGF-β (clone 1D11) or antibody control (clone SV5) were added at the indicated concentration. After an overnight incubation, cells were lysed and luciferase detected. Background as determined by wild-type TMLC (i.e. non-L-TGF-β/GARP expressing TMLC) was subtracted. Results are shown compared to conditions where no inhibitory antibody was added. Data represent three independent experiments. FIG. 4A shows that of humanized anti-β8 antibodies (humanized variable domains and CH1-3), HuC6D4F12 is more effective than HuC6D4 in blocking TGF-β activation, as measured by TMLC reporter cells expressing L-TGF-β1/GARP. Both HuC6D4 and HuC6D4F12 are more effective than a pan-anti-TGF-β inhibitor, 1D11. FIG. 4B shows that humanized (humanized variable domains and CH1, with murine IgG2a CH2/CH3) antibodies with heavy chain with the C6 VH1 (D to K) mutation expressed with light chain D4, or the light chain D4 VL1 (N to H) mutation expressed with heavy chain C6, have improved ability to inhibit TGF-β activation, as measured by TMLC reporter cells expressing L-TGF-β1/GARP, relative to wild type HuC6D4. The antibodies with either the C6 VH1 (D to K), or the D4 VL1 (N to H) mutations alone, are not as effective as HuC6D4F12, but more effective than wildtype HuC6D4.

FIG. 7A-C shows that HC6D4F12 effectively blocks tumor growth in a syngenic model of lung cancer (Lewis Lung Carcinoma cells stably transfected with mouse integrin β8 subunit). Shown are dose escalation cohorts consisting of mice with established β8 LLC tumors receiving antibodies (or isotype control (SV5) either 2, 5 or 10 mg/kg I.P. on days 5, and 12. Anti-SV5 is the IgG2a isotype control antibody. All mice were euthanized on day 14 and A) tumor volumes and B) tumor weights measured. In 7C, serum levels of each antibody were measured from the serum of individual mice by ELISA assay at endpoint on day 14, 48 hrs after the last injection of antibody. * p<0.05, ** p, 0.01 using Student's unpaired t-test.

FIG. 8A-C: Hu C6D4F12 binds with higher affinity to an overlapping epitope recognized by human ADWA11 2.4, and more effectively inhibits function. Gene synthesis of the humanized variable domains of anti-αvβ8 ADWA11 2.4 ((U.S. Patent Pub. No.: US 2020/0079855 A1)) was used to create a version of ADWA11 2.4 where the variable domains and CH1 domains were humanized and the CH1/CH2 domain were murine IgG2a. FIG. 8A, C: The CH1-3 domains of this chimeric version of ADWA11 2.4 were identical to HuC6D412 allowing direct comparison between these two antibodies for surface staining (A) or functional assays (C). FIG. 8B: a version of huC6D4F12, where CH1-3 were all human was used to compete with the chimeric ADWA11 2.4, which allowed specific detection of ADWA11 2.4 with anti-mouse (H+L) PE. All antibodies were produced in CHO cells. FIG. 8A: Cell surface binding is shown using ADWA11 2.4 and HuC6D4F12 to OVCAR3 cells, using anti-mouse (H+L)-PE as detection antibody. Primary antibodies were incubated at 4° C. for 15 min. FIG. 8B: ADWA11 2.4 (1 mg/ml) and different concentrations of fully human C6D4 F12 were allowed to bind to OVCAR3 cells at 4° C. for 15 min and after washing, detected using anti-mouse (H+L) PE as a detection antibody. FIG. 8C: ADWA11 2.4 and HuC6D4F12 were used to inhibit TGF-β activation using immobilized αvβ8 (1 µg/ml) and TGF-β1/GARP expressing TMLC reporter cells. Using this system the HuC6D4F12 had a dramatically enhanced ability (~77 fold) to block αvβ8 function relative to ADWA11 2.4.

DEFINITIONS

Figure 5:
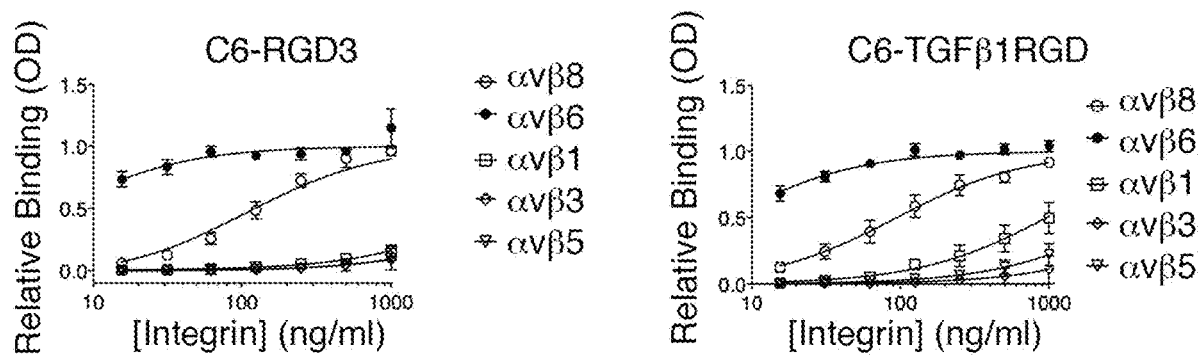
FIG. 5 depicts that C6-TGFβ1RGD binds to αvβ8, αvβ6 and αvβ1. The specificity of C6-RGD3 (left) for the 5 αv-integrins was compared with C6-TGFβ1RGD (right) in an ELISA assay. ELISA plates were coated with antibodies (2 µg/ml), washed, blocked with BSA, and then recombinant integrins were added at the indicated concentrations. After a brief incubation at RT, wells were washed and bound integrin detected with biotin conjugated anti-αv (8B8-biotin, 1 µg/ml) followed by Streptavidin-HRP.
Figure 6:
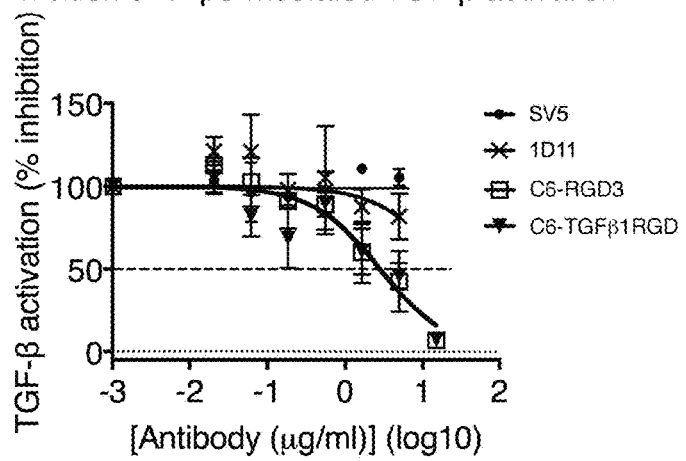
FIG. 6 shows C6-TGFβ1RGD is more efficient in blocking TGF-β activation than C6-RGD3 TGF-β reporter cells (TMLC) expressing L-TGF-β/GARP (15,000 cells) on their cell surface were applied to wells coated with recombinant αvβ8 (0.5 mg/ml coating concentration). C6-RGD3, C6-TGFβ1RGD, anti-pan TGF-β (clone 1D11) or antibody control (clone SV5) were added at the indicated concentrations. After an overnight incubation, cells were lysed and luciferase detected. Background as determined by wild-type TMLC (i.e. non-L-TGF-β/GARP expressing TMLC) was subtracted. Results are shown compared to conditions where no inhibitory antibody was added. Data represent three independent experiments.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

The terms "anti-αvβ8 antibody," "αvβ8 specific antibody," "αvβ8 antibody," and "anti-αvβ8" are used synonymously herein to refer to an antibody that specifically binds to αvβ8. Similarly, an anti-β8 antibody (and like terms) refer to an antibody that specifically binds to β8. The anti-αvβ8 antibodies and anti-β8 antibodies described herein bind to the protein expressed on αvβ8 expressing cells.

An αvβ8-associated disorder is a condition characterized by the presence of αvβ8-expressing cells, either cells expressing an increased level of αvβ8, or increased number of αvβ8-expressing cells relative to a normal, non-diseased control. TGFβ-associated disorders (disorders characterized by higher than normal TGFβ activity) include αvβ8-associated disorders, as αvβ8 is involved in activating TGFβ in certain circumstances, as described herein.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. As described below, the algorithms can account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "antibody" refers to a polypeptide comprising a framework region encoded by an immunoglobulin gene, or fragments thereof, that specifically bind and recognize an antigen, e.g., human αvβ8, a particular cell surface marker, or any desired target. Typically, the "variable region" contains the antigen-binding region of the antibody (or its functional equivalent) and is most critical in specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Antibodies described herein can be of any isotype of isotype class. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively. In some embodiments, the IgG is an IgG1, IgG2, IgG3 or IgG4.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., supra; Marks et al., *Biotechnology*, 10:779-783, (1992)).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some complementary determining region ("CDR") residues and possibly some framework ("FR") residues are substituted by residues from analogous sites in rodent antibodies.

Antibodies or antigen-binding molecules of the invention further includes one or more immunoglobulin chains that are chemically conjugated to, or expressed as, fusion proteins with other proteins. It also includes bispecific antibody. A bispecific or bifunctional antibody is an artificial hybrid antibody having two different heavy/light chain pairs and two different binding sites. Other antigen-binding fragments or antibody portions of the invention include bivalent scFv (diabody), bispecific scFv antibodies where the antibody molecule recognizes two different epitopes, single binding domains (dAbs), and minibodies.

The various antibodies or antigen-binding fragments described herein can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources.

A "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities.

As used herein, "V-region" refers to an antibody variable region domain comprising the segments of Framework 1, CDR1, Framework 2, CDR2, Framework 3, CDR3, and Framework 4. These segments are included in the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson and Wu, *Nucleic Acids Res.* 2000 Jan. 1; 28(1): 214-218 and Johnson et al., Nucleic Acids Res., 29:205-206 (2001); Chothia & Lesk, (1987) *J. Mol. Biol.* 196, 901-917; Chothia et al. (1989) Nature 342, 877-883; Chothia et al. (1992) J. Mol. Biol. 227, 799-817; Al-Lazikani et al., *J. Mol. Biol* 1997, 273(4)). Unless otherwise indicated, CDRs are determined according to Kabat. Definitions of antigen combining sites are also described in the following: Ruiz et al. *Nucleic Acids Res.*, 28, 219-221 (2000); and Lefranc *Nucleic Acids Res.* January 1; 29(1):207-9 (2001); MacCallum et al., *J. Mol. Biol.*, 262: 732-745 (1996); and Martin et al, *Proc. Natl Acad. Sci. USA*, 86, 9268-9272 (1989); Martin, et al, *Methods Enzymol.*, 203: 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *Proc. Natl. Acad. Sci. USA*, 81:6851-6855 (1984); Morrison and Oi, *Adv. Immunol.*, 44:65-92 (1988); Verhoeyen et al., *Science*, 239:1534-1536 (1988); Padlan, *Molec. Immun.*, 28:489-498 (1991); Padlan, *Molec. Immun.*, 31(3):169-217 (1994).

The antibody binds to an "epitope" on the antigen. The epitope is the specific antibody binding interaction site on the antigen, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The term "specifically bind" refers to a molecule (e.g., antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, an antibody that specifically binds β8 will typically bind to β8 with at least a 2-fold greater affinity than a non-β8 target (e.g., a different integrin subunit, e.g., β6).

The term "binds" with respect to a cell type (e.g., an antibody that binds fibrotic cells, hepatocytes, chondrocytes, etc.), typically indicates that an agent binds a majority of the cells in a pure population of those cells. For example, an antibody that binds a given cell type typically binds to at least ⅔ of the cells in a population of the indicated cells (e.g., 75, 80, 85, 90, 91, 92, 93, 94, 95, 96, 97, 98, 99, or 100%). One of skill will recognize that some variability will arise depending on the method and/or threshold of determining binding.

As used herein, a first antibody, or an antigen-binding portion thereof, "competes" for binding to a target with a second antibody, or an antigen-binding portion thereof, when binding of the second antibody with the target is detectably decreased in the presence of the first antibody compared to the binding of the second antibody in the absence of the first antibody. The alternative, where the binding of the first antibody to the target is also detectably decreased in the presence of the second antibody, can, but need not be the case. That is, a second antibody can inhibit the binding of a first antibody to the target without that first antibody inhibiting the binding of the second antibody to the target. However, where each antibody detectably inhibits the binding of the other antibody to its cognate epitope or ligand, whether to the same, greater, or lesser extent, the antibodies are said to "cross-compete" with each other for binding of their respective epitope(s). Both competing and cross-competing antibodies are encompassed by the present invention. The term "competitor" antibody can be applied to the first or second antibody as can be determined by one of skill in the art. In some cases, the presence of the competitor antibody (e.g., the first antibody) reduces binding of the second antibody to the target by at least 10%, e.g., 20%, 30%, 40%, 50%, 60%, 70%, 80%, or more, e.g., so that binding of the second antibody to target is undetectable in the presence of the first (competitor) antibody.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "diagnosis" refers to a relative probability that a disorder such as cancer or an inflammatory condition is present in the subject. Similarly, the term "prognosis" refers to a relative probability that a certain future outcome may occur in the subject. For example, prognosis can refer to the likelihood that an individual will develop a TGFβ or αvβ8 associated disorder, have recurrence, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, a TGFβ or αvβ8 associated disorder. In some embodiments, the sample may be a tissue biopsy, such as needle biopsy, fine needle biopsy, surgical biopsy, etc. The sample can also be a blood sample or blood fraction, e.g., white blood cell fraction, serum, or plasma. The sample can comprise a tissue sample harboring a lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

The terms "therapy," "treatment," and "amelioration" refer to any reduction in the severity of symptoms. In the case of treating an inflammatory condition, the treatment can refer to reducing, e.g., blood levels of inflammatory cytokines, blood levels of active mature TGFβ, pain, swelling, recruitment of immune cells, etc. In the case of treating cancer, treatment can refer to reducing, e.g., tumor size, number of cancer cells, growth rate, metastatic activity, cell death of non-cancer cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (no detectable symptoms remaining) or partial, such that symptoms are less frequent of severe than in a patient without the treatment described herein. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

"Cancer", "tumor," "transformed" and like terms include precancerous, neoplastic, transformed, and cancerous cells, and can refer to a solid tumor, or a non-solid cancer (see, e.g., Edge et al. *AJCC Cancer Staging Manual* ($7^{th}$ ed. 2009); Cibas and Ducatman *Cytology: Diagnostic principles and clinical correlates* ($3^{rd}$ ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, *Culture of Animal Cells a Manual of Basic Technique* ($3^{rd}$ ed. 1994)). Although transformation can arise from infection with a transforming virus and incorporation of new genomic DNA, or uptake of exogenous DNA, it can also arise spontaneously or following exposure to a carcinogen.

The term "cancer" can refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia (AML), chronic myeloid leukemia (CIVIL), and multiple myeloma. In some embodiments, the antibody compositions and methods described herein can be used for treating cancer.

The term "co-administer" refers to the simultaneous presence of two active agents in the blood of an individual. Active agents that are co-administered can be concurrently or sequentially delivered.

DETAILED DESCRIPTION OF THE INVENTION

The inventors have found new antibodies with higher affinity for αvβ8 compared to earlier-described antibodies.

Among the antibodies discovered are antibodies that bind with higher affinity than the C6D4 antibody (see, e.g., WO2018/064478) to αvβ8. Also discovered is an antibody comprising, instead of a standard light chain CDR1 containing a TGF-β3 RGD sequence, a light chain CDR1 containing the TGF-β1 RGD sequence with improved binding properties compared to RGD-containing antibodies as described in WO2018/064478.

Antibodies

Provided herein are antibodies that bind human (and in some embodiments other mammalian, e.g., such as mouse, guinea pig, pig, and rabbit) integrin αvβ8. In some embodiments, the antibodies are isolated, are chimeric (comprising at least some heterologous amino acid sequence), are labeled or covalently linked to another molecule such a cytotoxic agent or a combination thereof. In some embodiments, the antibodies specifically bind human integrin αvβ8 and block binding of a ligand to human integrin αvβ8. Exemplary ligands can include, for example, TGFβ and LAP.

The ability of an antibody to block αvβ8 integrin binding of a ligand can be determined by inhibition of binding of a soluble form of αvβ8 or a full-length form of αvβ8 expressed on the surface of cells to immobilized latent-TGF-beta or a portion thereof containing the sequence RGDL (SEQ ID NO: 60) See, e.g., Ozawa, A, et al. *J Biol Chem.* 291(22):11551-65 (2016).

The inventors have discovered that the previously-describe C6D4 antibody (see, e.g., WO2018/064478) can be further improved by the following D→K change in HCDR1, N→H change in LCDR1 or both.

Humanized C6D4 CDRs:

```
                             (SEQ ID NO: 1)
HCDR1:      TFTDYSMH (SEQ ID NO: 3)
HCDR2:      RINTETGEPTFADDFRG (SEQ ID NO: 38)
HCDR3:      FYYGRDT (SEQ ID NO: 5)
LCDR1:      KSSQSLLNSRSRKNYLA
```

```
                             (SEQ ID NO: 7)
LCDR2:      WASTRES (SEQ ID NO: 8)
LCDR3:      KQSYNLLS
```

Thus the new antibodies have the same CDRs as above but include a different HCDR1 (TFTKYSMH (SEQ ID NO:2)), a different LCDR1 (KSSQSLLHSRSRKNYLA (SEQ ID NO:6)), or both changes. In some embodiments the HCDR1 sequence can be SEQ ID NO:4, where the variable position can be S or T. In some embodiments, the antibody comprises the following heavy chain and light chain variable regions, respectively, where the bolded and underlined amino acid represents a change compared to the parent HuC6D4 antibody sequence:

```
                                               (SEQ ID NO: 9)
QIQLVQSGAEVKKPGASVKISCKASGYTFTKYSMHWVRQAPGQGLEWVAR

INTETGEPTFADDFRGRFTVTLDTSTSTAYLEIRSLRSDDTAVYFCAIFY

YGRDTWGQGTTLTVSS heavy chain variable region (SEQ ID NO:10)
EIVMTQSPATLSVSPGERVTMSCKSSQSLLHSRSRKNYLAWYQQKPGQAP

RLLIYWASTRESGVPARFSGSGSGTEFTLTISSVQSEDFAVYYCKQSYNL

LSFGQGTVLEIKR light chain variable region.
```

In some embodiments, the antibodies comprise the heavy chain CDR1, CDR2, and CDR3 sequences described above but contain 1, 2, or 3 conservative amino acid substitutions in one, two or more CDR sequences compared to those listed above, but includes the underlined and bolded amino acid (D→K change in HCDR1). In some embodiments, the antibodies comprise the light chain CDR1, CDR2, and CDR3 sequences described above but contain 1, 2, or 3 conservative amino acid substitutions in one, two or more CDR sequences compared to those listed above, but includes the underlined and bolded amino acid (N→H change in LCDR1).

In some embodiments, an antibody as described herein (e.g., having the CDRs specified above) comprises one, two, three or all four of the framework sequences as provided here:

| Frameworks | Fr 1 (SEQ ID NO:) | Fr2 (SEQ ID NO:) |
|---|---|---|
| H | (Q)IQL(L)(Q)SGPELKKPGETVKISCKASGY (13)<br>E  M  E<br>Where (X) can be specified AA | WVKQAPGKGLKW(V)A (14)<br>M |
| L | (D)IVM(T)QSPSSLAV(S)AGE(K)VT(M)SC (15)<br>E     S         P   N  V<br>Where (X) can be specified AA all<br>alternatives listed under | WYQQKPGQSP(R)LLIY (16)<br>K |

| Frameworks | Fr3 (SEQ ID NO:) | Fr4 (SEQ ID NO:) |
|---|---|---|
| H | RFA(V)SLETSASTAYLQINNLKNEDTATYFCAI (17)<br>F | WGQGTT(L)TVSS (18<br>V |
| L | GVPDRFTGSGSGTDFTLTISSVQAEDLAVY(Y)C (19)<br>F | FGAGT(K)LE(L)K (20)<br>R   I |

In some embodiments, an antibody as described herein comprises one, two, three or all four of the framework sequences as provided here:

| Frameworks | Fr 1 (SEQ ID NO:) | Fr2 (SEQ ID NO:) |
|---|---|---|
| H | QIQLVQSG(P)(E)(L)KKPG(E)(T)VKISCKASGYTFT (21)<br>        A  K V      A S<br>Where (X) can be specified AA | WV(K)QAPG(K)GL(K)WVA (22)<br>   R      Q    E |
| L | (D)IVMTQ(S)P(S)(S)L(A)VS(A)GE(K)VTMSC (23)<br>  E      T    A T  S    P    R<br>                 V | WYQQKPGQSPRLLIY (24) |

| Frameworks | Fr3 (SEQ ID NO:) | |
|---|---|---|
| H | RF(A)V(S)L(E)TS(A)STAYL(Q)I(N)(N)L(K)(N)(E)DTA(T)YFCAI (25)<br>   T  T  D    T       E   R  S  R S D    V<br>   S               T<br>Where X can be specified AA all alternatives listed under | |
| L | (G)VP(D)RF(T)GSGSGT(D)FTLTISSVQ(A)ED(L)AVYYC (26)<br>  D      A    S         E          S    F | |

| Frameworks | Fr4 (SEQ ID NO:) | |
|---|---|---|
| H | WGQGT(T)LTVSS (27)<br>      A | |
| L | FG(A)GT(K)LE(L)KR (28)<br>   Q    V   I | |

In some embodiments, an antibody as described herein comprises one, two, three or all four of the framework sequences as provided here:

| Frameworks | Fr 1 (SEQ ID NO:) | Fr2 (SEQ ID NO:) |
|---|---|---|
| H | QIQL(V)QSG(P)(E)(L)KKPG(E)(T)VKISCKASGYTFT (29)<br>    L       A K V      A S<br>Where (X) can be specified AA | WV(K)QAPG(K)GL(K)W(V)(A) (30)<br>   R      Q    E  M G |
| L | (D)IVM(T)Q(S)P(S)(S)L(A)VS(A)GE(K)VTMSC (31)<br>  E     S    T  A T  S  P    R<br>              V        I | WYQQKPGQ(S)PRLLIY (32)<br>        A |

| Frameworks | Fr3 (SEQ ID NO:) | |
|---|---|---|
| H | RF(A)(V)(S)L(E)TS(A)(S)TA(Y)L(Q)I(N)(N)L(K)(N)(E)DTA(T)YFCAI (33)<br>   T F T  D    T T    N   E   R  S  R S D    V<br>   S                 I                       K<br>                    T<br>Where (X) can be specified AA all alternatives listed under | |
| L | (G)VP(D)RF(T)GSGSGT(D)FTLTISSVQ(A)ED(L)AVYYC (34)<br>  D    A    S        E         S    F<br>                               D | |

| Frameworks | Fr4 (SEQ ID NO:) | |
|---|---|---|
| H | WGQGT(T)LTVSS (35)<br>      A | |
| L | FG(A)GT(K)LE(I)KR (36)<br>   Q    V    L | |

In some embodiments, any antibody described herein or as described in WO2018/064478 can comprise a light chain CDR1 comprising a RGD sequence from TGF-β3, for example GRGDLGRLKK (SEQ ID NO: 61). In some embodiments, the light chain CDR1 is the previous sequence inserted into the C6D4 LCDR1 such that the LCDR1 comprises KSSQSLLRRGDLATIHGNALA (SEQ ID NO: 11). Thus, for example, an antibody that binds αvβ8 as well as αvβ6 can comprise the following CDRs: a heavy chain complementary determining region (HCDR) 1 comprising TFTDYSMH (SEQ ID NO:1) or TFTKYSMH (SEQ ID NO:2); a HCDR 2 comprising RINTETGEPTFADDFRG (SEQ ID NO:3); a HCDR 3 comprising FYYGRD(S/T) (SEQ ID NO:4); and a light chain complementary determining region (LCDR) 1 comprising KSSQSLLRRGD-LATIHGNALA (SEQ ID NO:11); a LCDR2 comprising WASTRES (SEQ ID NO:7); and a LCDR3 comprising KQSYNLLS (SEQ ID NO:8).

The structure of the C6 HCDR1 as shown in FIG. 1 illustrates the contact of HCDR1 D31 with integrin β8 residues R201, Q202, and K203 indicating that the C6 heavy chain (see, e.g., WO2018/064478) with the D→K change in HCDR1 (SEQ ID NO:2) with improved affinity to αvβ8 would also improve the ability of antibodies to bind and block function of αvβ8 when combined with the light chain of antibodies with CDR1 comprising a RGD sequence from TGF-β3, as previously claimed in WO2018/064478, for example, the LCDR1 sequence KSSQSLLGRGDLGRLK-KNALA (SEQ ID NO:40), SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, or SEQ ID NO:59. For example, in view of the improved activity resulting from inclusion of SEQ ID NO:2 in HCDR1, in some embodiments, the antibody can comprise heavy chain CDRs 1, 2, 3 as SEQ ID NO:2, SEQ ID NO:3 and SEQ ID NO:4 respectively, and light chain CDRs 2 and 3 as SEQ ID NO:7 and SEQ ID NO:8 and light chain CDR1 selected from a LCDR of WO2018/064478, which can include but is not limited to SEQ ID NO:40.

Framework regions can be selected in some embodiments from SEQ ID NOS: 13-36 as depicted above. In some embodiments the light chain variable region is SEQ ID NO:12. In some embodiments, the heavy chain variable region is SEQ ID NO: 9 the improved C6D4 heavy chain variable region as described herein) or SEQ ID NO: 37 (the original C46D4 heavy chain variable region as depicted for example in WO2018/064478 or humanized versions thereof.

For preparation and use of suitable antibodies as described herein, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946, 778, 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633, 425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody as described herein can also be produced in various formats, including as a Fab, a Fab', a $F(ab')_2$, a scFv, or a dAB. The antibody fragments can be obtained by a variety of methods, including, digestion of an intact antibody with an enzyme, such as pepsin (to generate $(Fab')_2$ fragments) or papain (to generate Fab fragments); or de novo synthesis. Antibody fragments can also be synthesized using recombinant DNA methodology. In some embodiments, an anti-β8 antibody comprises $F(ab')_2$ fragments that specifically bind β8. An antibody of the invention can also include a human constant region. See, e.g., Fundamental Immunology (Paul ed., 4d ed. 1999); Bird, et al., *Science* 242:423 (1988); and Huston, et al., *Proc. Natl. Acad. Sci. USA* 85:5879 (1988).

Methods for humanizing or primatizing non-human antibodies are also known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007). The antibody or antibody fragment can also be labeled, or conjugated to a therapeutic agent as described below.

The specificity of antibody binding can be defined in terms of the comparative dissociation constants (Kd) of the antibody for the target (e.g., β8) as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target.

The desired affinity for an antibody, e.g., high (pM to low nM), medium (low nM to 100 nM), or low (about 100 nM or higher), may differ depending upon whether it is being used as a diagnostic or therapeutic. For example, an antibody with medium affinity may be more successful in localizing to desired tissue as compared to one with a high affinity. Thus, antibodies having different affinities can be used for diagnostic and therapeutic applications.

A targeting moiety will typically bind with a Kd of less than about 1000 nM, e.g., less than 250, 100, 50, 20 or lower nM. In some embodiments, the Kd of the affinity agent is less than 15, 10, 5, or 1 nM. In some embodiments, the Kd is 1-100 nM, 0.1-50 nM, 0.1-10 nM, or 1-nM. The value of the dissociation constant (Kd) can be determined by well-known methods, and can be computed even for complex mixtures by methods as disclosed, e.g., in Caceci et al., Byte (1984) 9:340-362.

Affinity of an antibody, or any targeting agent, for a target can be determined according to methods known in the art, e.g., as reviewed in Ernst et al. Determination of Equilibrium Dissociation Constants, *Therapeutic Monoclonal Antibodies* (Wiley & Sons ed. 2009).

Quantitative ELISA, and similar array-based affinity methods can be used. ELISA (Enzyme linked immunosorbent signaling assay) is an antibody-based method. In some cases, an antibody specific for target of interest is affixed to a substrate, and contacted with a sample suspected of containing the target. The surface is then washed to remove unbound substances. Target binding can be detected in a variety of ways, e.g., using a second step with a labeled antibody, direct labeling of the target, or labeling of the primary antibody with a label that is detectable upon antigen binding. In some cases, the antigen is affixed to the substrate (e.g., using a substrate with high affinity for proteins, or a Strepavidin-biotin interaction) and detected using a labeled antibody (or other targeting moiety). Several permutations of the original ELISA methods have been developed and are known in the art (see Lequin (2005) *Clin. Chem.* 51:2415-18 fora review).

The Kd, Kon, and Koff can also be determined using surface plasmon resonance (SPR), e.g., as measured by using a Biacore T100 system or using kinetic exclusion assays (e.g., KinExA®). SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given frequency is shined on the surface, the changes to the optical reflectivity of the gold indicate binding, and the kinetics of binding. Kinetic exclusion assays is the preferred method to determine affinity unless indicated otherwise. This technique is described in, e.g. Darling et al., *Assay and Drug Development Technologies* Vol. 2, number 6 647-657 (2004).

Binding affinity can also be determined by anchoring a biotinylated interactant to a streptavidin (SA) sensor chip. The other interactant is then contacted with the chip and detected, e.g., as described in Abdessamad et al. (2002) *Nuc. Acids Res.* 30:e45.

Also provided are polynucleotides (e.g., DNA or RNA) encoding the antibodies described herein, or binding fragments thereof comprising at least heavy chain or light chain CDRs or both, e.g., polynucleotides, expression cassettes (e.g., a promoter linked to a coding sequence), or expression vectors encoding heavy or light chain variable regions or segments comprising the complementary determining regions as described herein. In some embodiments, the polynucleotide sequence is optimized for expression, e.g., optimized for mammalian expression or optimized for expression in a particular cell type.

Methods of Treatment

The anti-αvβ8 antibodies described herein (including αvβ8 binding fragments thereof, labeled antibodies, immunoconjugates, pharmaceutical compositions, etc.) as well as antibodies that bind both αvβ8 and αvβ6 as described herein or binding fragments thereof can be used to detect, treat, ameliorate, or prevent chronic obstructive pulmonary disease (COPD) and asthma, inflammatory bowel disease, inflammatory brain autoimmune disease, multiple sclerosis, a demyelinating disease (e.g., transverse myelitis, Devic's disease, Guillain-Barré syndrome), neuroinflammation, kidney disease, or glioma, arthritis, fibrotic disorders, such as airway fibrosis, idiopathic pulmonary fibrosis, non-specific interstitial pneumonia, post-infectious lung fibrosis, diffuse alveolar damage, collagen-vascular disease associated lung fibrosis, drug-induced lung fibrosis, silicosis, asbestos-related lung fibrosis, respiratory bronchiolitis, respiratory bronchiolitis interstitial lung disease, desquamative interstitial fibrosis, cryptogenic organizing pneumonia, chronic hypersensitivity pneumonia, drug-related lung or hepatic fibrosis, renal fibrosis, and liver fibrosis (e.g., induced by alcohol, drug use, steatohepatitis, viral infection (e.g., hepatitis B or C), cholestasis, etc., and cancer, including but not limited to adenocarcinoma, squamous carcinoma, breast carcinoma, and cancer growth and metastasis. Accordingly, the antibodies and pharmaceutical compositions described herein can be administered to a human having or suspected of having one of the above-listed diseases in an appropriate dosage to ameliorate or treat one of the disease or at least one symptom thereof.

Without intending to limit the scope of the invention, in some embodiments it is believed that antibodies described herein function in part by triggering an increase in WWII expression in antigen presenting cells.

Moreover, the anti-αvβ8 antibodies described herein (including αvβ8 binding fragments thereof, labeled antibodies, immunoconjugates, pharmaceutical compositions, etc.) can be used to treat, ameliorate, or prevent viral infections (e.g., by stimulating an immune response). Exemplary viral infections include but are not limited to hepatitis A, B (HBV), and C (HCV), herpes simplex virus (e.g., HSVI, HSVII), HIV, and influenza infections, all of which are enhanced by Treg-mediated immune suppression (Keynan, Y, et al., *Clin Infect Dis.* 2008 Apr. 1; 46(7):1046-52.

Also provided are pharmaceutical compositions comprising the present anti-αvβ8 antibodies or antigen-binding molecules as well as antibodies that bind both αvβ8 and αvβ6 as described herein or binding fragments thereof, either of which can be formulated together with a pharmaceutically acceptable carrier. The compositions can additionally contain other therapeutic agents that are suitable for treating or preventing a given disorder. Pharmaceutically carriers can enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition as described herein can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, intranasal, inhalational, spinal or epidermal administration (e.g., by injection or infusion). Depending on the route of administration, the active compound, i.e., antibody, may be coated in a material to protect the compound from the action of acids and other natural conditions that may inactivate the compound.

The antibodies, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions of the present invention. Applicable methods for formulating the antibodies and determining appropriate dosing and scheduling can be found, for example, in *Remington: The Science and Practice of Pharmacy,* $21^{st}$ Ed., University of the Sciences in Philadelphia, Eds., Lippincott Williams & Wilkins (2005); and in *Martindale: The Complete Drug Reference*, Sweetman, 2005, London: Pharmaceutical Press., and in Martindale, *Martindale: The Extra Pharmacopoeia,* 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of the anti-αvβ8 antibody is employed in the pharmaceutical compositions of the invention. The anti-αvβ8 antibodies are formulated into pharmaceutically acceptable dosage forms by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

In some embodiments, the pharmacological compositions comprise a mixture of the anti-αvβ8 antibody or antigen binding molecule (e.g. that blocks ligand binding or blocks activation by ligand binding) and a second pharmacological agent. Without intending to limit the invention, it is noted that the inventors have found that thymic stromal lymphopoietin (TSLP) is an inducer of viral clearance in a mouse model of acute and chronic HBV and thus is useful to combine TSLP with an αvβ8 antibody for anti-viral treatments. Moreover, the inventors have found that OX40 agonists are effective in stimulating an immune response to HBV in combination with an αvβ8 antibody.

As an alternative to mixing the anti-αvβ8 antibody and second pharmacological agent in a pharmacological composition, the anti-αvβ8 antibody and second pharmacological agent can be separately administered to the human in need thereof within a time frame (e.g., within 3, 2, o 1 day or within 24, 13, 6, or 3 hours of each other).

Diagnostic Compositions and Applications

Integrin αvβ8 is expressed on fibroblasts, stellate cells, chondrocytes, activated macrophages and subsets of T and B-cells. Integrin αvβ8 is increased in expression in fibroblasts in COPD and pulmonary fibrosis, and can be used as a surrogate marker for increased fibroblast cell mass. Thus the presently disclosed antibodies can be broadly applicable to bioimaging strategies to detect fibroinflammatory processes. The presently described therapeutic and diagnostic antibodies can be applied to: inflammatory bowel disease (IBD), chronic obstructive pulmonary disease (COPD), asthma, arthritis, a hepatic fibroinflammatory disorder, alcohol induced liver injury, non-alcoholic steatohepatitis (NASH), viral hepatitis, and primary biliary cirrhosis (PBC), graft rejection after liver transplantation, autoimmune hepatitis, an autoimmune disorder, lupus erythematosus, scleroderma, dermatomyositis, bullous pemphigoid, pemphigus vulgaris, a pulmonary fibrotic disorder, an inflammatory brain autoimmune disease, multiple sclerosis, a demyelinating disease, neuroinflammation, kidney disease, glomerulonephritis, hepatocellular carcinoma (HCC), adenocarcinoma, squamous carcinoma, glioma, melanoma, prostate, ovarian, uterine and breast carcinoma.

β8 and PD-L1 expression inversely correlate. Thus, anti-αvβ8 antibodies described herein can be used as a marker for PD-L1 expression and optionally for selecting individuals most likely to benefit from anti-αvβ8 treatment.

Anti-αvβ8 antibodies described herein (including αvβ8 binding fragments thereof, affinity matured variants, or scFvs) can be used for diagnosis, either in vivo or in vitro (e.g., using a biological sample obtained from an individual).

When used for detection or diagnosis, the antibody is typically conjugated or otherwise associated with a detectable label. The association can be direct e.g., a covalent bond, or indirect, e.g., using a secondary binding agent, chelator, or linker.

A labeled antibody can be provided to an individual to determine the applicability of an intended therapy. For example, a labeled antibody may be used to detect the integrin β8 density within a diseased area. For therapies intended to target TGFβ or αvβ8 activity (to reduce TGFβ or αvβ8 activity), the density of β8 is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MM, PET scanning, etc.). Such in vivo methods can be carried out using any of the presently disclosed antibodies.

Any of the presently disclosed antibodies can also be used for in vitro diagnostic or monitoring methods, e.g., using cells or tissue from a patient sample. In some embodiments, labeled F9 (or a β8 binding fragment or affinity-matured variant) is used, as it can bind fixed cells as well as non-fixed cells.

In some embodiments, the diagnostic antibody is a single-chain variable fragment (scFv). Intact antibodies (e.g., IgG) can be used for radioimmunotherapy or targeted delivery of therapeutic agents because they exhibit high uptake and retention. In some cases, the persistence in circulation of intact mAbs can result in high background (Olafsen et al. (2012) *Tumour Biol.* 33:669-77; Cai et al. (2007) *J Nucl Med.* 48:304-10). ScFvs, typically with a molecular mass of ~25 kD, are rapidly excreted by the kidneys, but are monovalent and can have lower affinity. The issues of monovalency can be overcome with advanced antibody engineering (as shown herein), where affinities can be improved to the low nM to pM range. Such antibodies have short enough half-lives to be useful as imaging agents and have suitable binding characteristics for tissue targeting (Cortez-Retamozo et al. (2004) *Cancer Res.* 64:2853-7). As shown herein, we have created a very high affinity scFV antibody derivatives of 4F1, 6B9, called F9, that can be converted to humanized scFV platforms. These improved antibodies are not function blocking, and thus can be used in combination with a therapeutic agent that targets β8.

A diagnostic agent comprising an antibody described herein can include any diagnostic agent known in the art, as provided, for example, in the following references: Armstrong et al., *Diagnostic Imaging*, 5th Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). The terms "detectable agent," "detectable moiety," "label," "imaging agent," and like terms are used synonymously herein. A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. PET is particularly sensitive and quantitative, and thus valuable for characterizing fibrotic processes in vivo (Olafsen et al. (2012) *Tumour Biol.* 33:669-77; Cai et al. (2007) *J Nucl Med.* 48:304-10). This is useful beyond a companion diagnostic and would be generally useful to diagnose, clinically stage and follow fibrotic patients during any treatment regimen.

A radioisotope can be incorporated into the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cn, $^{64}$Cn, $^{67}$Cn, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed.*: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8,11-tetraazacyclotetradec-1-yl)methyl] benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra(methylene phosphonic acid) (DOTP), 1,4,8,11-tetraazacyclotetradecane-1,4,8,11-tetraacetic acid (TETA), 1,4,7,10-tetraazacyclododecane-1,4,7,10-tetraacetic acid (DOTA), N1,N1-bis(pyridin-2-ylmethyl)ethane-1,2-diamine (ENPy2) and derivatives thereof.

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives.

EXAMPLES

The following examples are offered to illustrate, but not to limit the claimed invention.

Example 1

The primers listed below had degenerate positions in select amino acids, which the structure predicted could be modified to generate new interactions with the integrin β8 subunit compared to antibody C6D4 (WO2018/064478). Four distinct primer pairs were used (called 1F/1R; 2F/2R; 3F/3R; 4F/4R) to amplify respectively CDRVH1, VK1, VK2 and VK3, which contained respectively, 2, 2, 2 and 1 degenerate positions.

These PCR fragments were joined by splice overlap extension PCR and then amplified using a flanking primer to create 5' and 3' overhangs. The library with its degenerate positions was verified by sequencing and then inserted into the yeast display vector pYD4 using gap-repair.

After induction of scFv expression, the scFv displayed yeast library was sorted using the recombinant αvβ8 ectodomain as antigen at varied concentrations for each round, and also using the reaction conditions that favor a fast on rate (Kon) and slow off rate (Koff). Briefly, yeast displayed scFv were allowed to react with the antigen to equilibrate for 1~30 minutes, and after extensive FACS buffer washing, the antigens were allowed to dissociate from yeast surface for 6~8 hours at room temperature, then the yeast bound αvβ8 was detected using an anti-human αv antibody followed by a secondary fluorophore conjugated antibody. Clones with the brightest mean fluorescence intensity were collected from each round of sorting, and incubated for growth then induced for next round of sorting. Single colonies were picked and individual clones identified by plasmid DNA and PCR fragment sequencing after $5^{th}$ round of sorting.

A summary of the changes is shown below (SEQ ID NOS 62, 37, 9, 63-64, and 10, respectively, in order of appearance):

| VH | Framework 1 | CDR1 | Framework 2 | CDR2 | Framework 3 | CDR3 | Framework 4 | scFv KD (nM) |
|---|---|---|---|---|---|---|---|---|
| C6D4 | QIQLVQSGPELKKPG ETVKISCKASGYTFT | DYSMH | WVKQAPGKGLKWVA | RINTETGEP TFADDFRG | RFAVSLETSASTAYLQ INNLKNEDTATYFCAI | FYYG RDS | WGQGTT LTVSS | 7.25 |
| HuC6D4 | QIQLVQSGAEVKKPG ASVKISCKASGYTFT | DYSMH | WVRQAPGQGLEWVA | RINTETGEP TFADDFRG | RFTVTLDTSTSTAYLE IRSLRSDDTAVYFCAI | FYYG RDT | WGQGTT LTVSS | 1.05 |
| HuC6D4F12 | QIQLVQSGAEVKKPG ASVKISCKASGYTFT | KYSMH | WVRQAPGQGLEWVA | RINTETGEP TFADDFRG | RFTVTLDTSTSTAYLE IRSLRSDDTAVYFCAI | FYYG RDT | WGQGTT LTVSS | 0.39 |

| VK | Framework 1 | CDR1 | Framework 2 | CDR2 | Framework 3 | CDR3 | Framework 4 | scFv KD (nM) |
|---|---|---|---|---|---|---|---|---|
| C6D4 | DIVMTQSPSSLAVSA GEKVTMSC | KSSQSLLNS RTRKNYLA | WYQQKPGQSPRLLIY | WASTRES | GVPDRFTGSGSGTDFT LTISSVQAEDLAVYYC | KQSY NLLS | FGAGTK LELKR | 7.25 |
| HuC6D4 | EIVMTQSPATLSVSP GERVTMSC | KSSQSLLNS RSRKNYLA | WYQQKPGQAPRLLIY | WASTRES | GVPARFSGSGSGTEFT LTISSVQSEDFAVYYC | KQSY NLLS | FGQGTV LEIKR | 1.05 |
| HuC6D4F12 | EIVMTQSPATLSVSP GERVTMSC | KSSQSLLHS RSRKNYLA | WYQQKPGQAPRLLIY | WASTRES | GVPARFSGSGSGTEFT LTISSVQSEDFAVYYC | KQSY NLLS | FGQGTV LEIKR | 0.39 |

Eleven of 16 clones with readable sequences had the same mutations in CDRVH1 (D to K) and CDRVK1 (N to H).

Primers used to make new library:

Oligo Name: Primer 1F
Sequence:
(SEQ ID NO: 65)
GGT TAT ACC TTC ACA VAN TAT WCT ATG CAT TGG GTT AG Oligo Name: Primer 1R
Sequence:
(SEQ ID NO: 66)
CTA ACC CAA TGC ATA GWA TAN TBT GTG AAG GTA TAA CC Oligo Name: Primer 2F
Sequence:
(SEQ ID NO: 67)
CAC AAT CGT TGT TAM ATT CAA GAW YKA GAA AGA ATT ATT TGG CTT GG Oligo Name: Primer 2R
Sequence:
(SEQ ID NO:68)
CCA AGC CAA ATA ATT CTT TCT MRW TCT TGA ATK TAA CAA CGA TTG TG Oligo Name: Primer 3F
Sequence:
(SEQ ID NO: 69)
CCA AGA TTG TTA ATC KAN WRG GCA TCT ACA AGA GAA TCA G Oligo Name: Primer 3R
Sequence:
(SEQ ID NO: 70)
CTG ATT CTC TTG TAG ATG CCY WNT MGA TTA ACA ATC TTG G Oligo Name: Primer 4F
Sequence:
(SEQ ID NO: 71)
GAT TTC GCA GTT TAC TAT TGC MAN CAA TCA TAC AAC TTA TTA TCA TTC GG

```
Oligo Name: Primer 4R
Sequence:
                                                  (SEQ ID NO: 72)
CCG AAT GAT AAT AAG TTG TAT GAT TGN TKG CAA TAG

TAA ACT GCG AAA TC

Oligo Name: 5 scFV F
Sequence:
                                                  (SEQ ID NO: 73)
GGT GGA GGC GGT TCC GG Oligo Name: 3 scFV R
Sequence:
                                                  (SEQ ID NO: 74)
CAA TGG TGA TGG TGA TGA TGA CCG TAC
```

As shown in FIG. 3A-D HuC6D4F12 is highly specific for αvβ8 and in FIG. 4A-B, HuC6D4F12, as well as either single mutation, is more efficient in blocking TGF-β activation than HuC6D4

Example 2

The D4 CDR L1 Vk was substituted to include the RRGDLATIHG motif (SEQ ID NO: 75) from human TGF-β1. Thus generated antibody has the same light chain and heavy chain CDRs and heavy chain and light chain variable regions as antibody HuC6D4 except for the change noted above (also depicted in FIG. 1). The resulting antibody was designated "C6-TGFβ1RGD". Thus, the Vk variable region of C6-TGFβ1RGD comprises SEQ ID NO:12 and the Vh variable region comprises SEQ ID NO:37.

The binding of C6-TGFβ1RGD was compared with C6-RGD3 (formerly described in WO2018/064478). FIG. 5 depicts an ELISA assay demonstrating a different binding preference of C6-TGF-β1RGD compared to C6-RGD3 where C6-TGF-β1RGD binds to αvβ1 in addition to αvβ8 and αvβ6. C6-TGFβ1RGD binds similarly to αvβ8 and αvβ6 as C6-RGD3. Each well was coated with antibodies (2 μg/ml), blocked with 1% BSA, washed in PBS, recombinant integrin αvβ8 (upper panel) and αvβ6 (lower panel) were added in varying concentrations (1000 ng/ml to 16 ng/ml) and after binding and washing were detected by anti-αv (8B8-biotin (1 μs/ml) followed by Streptavidin-HRP (n=3)).

FIG. 6 shows C6-TGFβ1RGD is more efficient in blocking TGF-β activation than C6-RGD3.

Affinity for the antibodies described in the Examples was determined using a kinetic exclusion assay format, KinExA (https://www.sapidyne.com). The affinity was calculated as follows:

C6D4 IgG 2a: 1.30 nM (95% CI: 1.40 nM-1.21 nM)
Human C6D4: 82.09 pM (95% CI: 95.74 pM-69.60 pM)
HuC6D4 F12: 2.36 pM (95% CI: 4.06 pM-1.04 pM)

| SEQUENCES |
|---|
| TFTDYSMH (SEQ ID NO: 1) |
| TFTKYSMH (SEQ ID NO: 2) |
| RINTETGEPTFADDFRG (SEQ ID NO: 3) |
| FYYGRD(S/T) (SEQ ID NO: 4) |
| KSSQSLLNSRSRKNYLA (SEQ ID NO: 5) |
| KSSQSLLHSRSRKNYLA (SEQ ID NO: 6); |

-continued

| SEQUENCES |
|---|
| WASTRES (SEQ ID NO: 7) |
| KQSYNLLS (SEQ ID NO: 8) |
| QIQLVQSGAEVKKPGASVKISCKASGYTFTKYSMHWVRQAPGQGLEWVARINTETGEPTFADDFRGRFTVTLDTSTSTAYLEIRSLRSDDTAVYFCAIFYYGRDTWGQGTTLTVSS (SEQ ID NO: 9) heavy chain variable region |
| EIVMTQSPATLSVSPGERVTMSCKSSQSLLHSRSRKNYLAWYQQKPGQAPRLLIYWASTRESGVPARFSGSGSGTEFTLTISSVQSEDFAVYYCKQSYNLLSFGQGTVLEIKR (SEQ ID NO: 10) light chain variable region |
| KSSQSLLRRGDLATIHGNALA (SEQ ID NO: 11) a light chain complementary determining region (LCDR) 1 comprising RGDL (SEQ ID NO: 60) |
| EIVMTQSPATLSVSPGERVTMSCKSSQSLLRRGDLATIHGNALAWYQQKPGQAPRLLIYWASTRESGVPARFSGSGSGTEFTLTISSVQSEDFAVYYC KQSYNLLSFGQGTVLEIKR (SEQ ID NO: 12) light chain variable region comprising RGDL (SEQ ID NO: 60) |
| SEQ ID NOS: 13-36 in tables above. |
| QIQLVQSGAEVKKPGASVKISCKASGYTFTDYSMHWVRQAPGQGLEWVARINTETGEPTFADDFRGRFTVTLDTSTSTAYLEIRSLRSDDTAVYFCAIFYYGRDTWGQGTTLTVSS (SEQ ID NO: 37) C6D4 heavy chain variable region-matched with SEQ ID NO: 12 to form C6-TGFβ1RGD |
| HuC4D6 HCDR3: FYYGRDT (SEQ ID NO: 38) |
| EIVMTQSPATLSVSPGERVTMSC KSSQSLLGRGDLGRLKKNALA WYQQKPGQAPRLLIY WASTRES GVPARFSGSGSGTEFTLTISSVQSEDFAVYYC KQSYNLLS FGQGTVLEIKR (SEQ ID NO: 39) |
| KSSQSLLGRGDLGRLKKNALA (SEQ ID NO: 40) |
| KSSQSLLNSRSRKNYLA (SEQ ID NO: 41) |
| KSSQSLLNSGRGDLGNALA (SEQ ID NO: 42) |
| KSSQSLLGRGDLGRLKKQKDHNALA (SEQ ID NO: 43) |
| KSSQSLLGRGDLGRLKKQKDNALA (SEQ ID NO: 44) |
| KSSQSLLGRGDLGRLKKQKNALA (SEQ ID NO: 45) |
| KSSQSLLGRGDLGRLKKQNALA (SEQ ID NO: 46) |
| KSSQSLLGRGDLGRLKKNALA (SEQ ID NO: 47) |
| KSSQSLLGRGDLGRLKNALA (SEQ ID NO: 48) |
| KSSQSLLGRGDLGRLNALA (SEQ ID NO: 49) |
| KSSQSLLGRGDLGRNALA (SEQ ID NO: 50) |
| KSSQSLLGRGDLGNALA (SEQ ID NO: 51) |
| KSSQSLLGRGDLGRLKKQKDHH (SEQ ID NO: 52) |
| KSSQSLLGRGDLGRLKKQKDH (SEQ ID NO: 53) |
| KSSQSLLGRGDLGRLKKQKD (SEQ ID NO: 54) |
| KSSQSLLGRGDLGRLKKQK (SEQ ID NO: 55) |
| KSSQSLLGRGDLGRLKKQ (SEQ ID NO: 56) |
| KSSQSLLGRGDLGRLKK (SEQ ID NO: 57) |

SEQUENCES

KSSQSLLGRGDLGRLK (SEQ ID NO: 58)

KSSQSLLGRGDLGRL (SEQ ID NO: 59)

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of enhancing an immune response to a viral infection in a human individual, the method comprising administering a sufficient amount of an antibody that specifically binds human αvβ8 to the individual, wherein the antibody comprises:
   a heavy chain complementary determining region (HCDR) 1 comprising TFTDYSMH (SEQ ID NO:1) or TFTKYSMH (SEQ ID NO:2);
   a HCDR 2 comprising RINTETGEPTFADDERG (SEQ ID NO:3);
   a HCDR 3 comprising FYYGRD (S/T) (SEQ ID NO:4);
   a light chain complementary determining region (LCDR) 1 comprising KSSQSLLNSRSRKNYLA (SEQ ID NO:5) or KSSQSLLHSRSRKNYLA (SEQ ID NO:6);
   a LCDR2 comprising WASTRES (SEQ ID NO:7); and
   a LCDR3 comprising KQSYNLLS (SEQ ID NO:8), wherein the antibody comprises one or none of SEQ ID NO: 1 and SEQ ID NO:5, but not both of SEQ ID NO: 1 and SEQ ID NO:5, thereby enhancing an immune response to the viral infection.

2. The method of claim 1, wherein the HCDR1 comprises SEQ ID NO:2 and the LCDR1 comprises SEQ ID NO:6.

3. The method of claim 1, wherein the HCDR1 comprises SEQ ID NO:1 and the LCDR1 comprises SEQ ID NO:6.

4. The method of claim 1, wherein the HCDR1 comprises SEQ ID NO:2 and the LCDR1 comprises SEQ ID NO:5.

5. The method of claim 1, comprising a heavy chain variable region comprising SEQ ID NO:9.

6. The method of claim 1, comprising a light chain variable region comprising SEQ ID NO: 10.

7. The method of claim 1, wherein the antibody is humanized.

8. The method of claim 1, wherein the antibody is linked to a detectable label.

9. The method of claim 1, wherein the viral infection is a hepatitis infection.

10. The method of claim 1, wherein the viral infection is a hepatitis B infection.

* * * * *